US008268849B2

(12) United States Patent
Kador et al.

(10) Patent No.: US 8,268,849 B2
(45) Date of Patent: Sep. 18, 2012

(54) MULTIFUNCTIONAL ANTIOXIDANTS AND METHODS OF USE THEREOF

(75) Inventors: Peter F. Kador, Omaha, NE (US); Hongxia Jin, Shanghai, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 942 days.

(21) Appl. No.: 12/237,936

(22) Filed: Sep. 25, 2008

(65) Prior Publication Data

US 2009/0105269 A1 Apr. 23, 2009

Related U.S. Application Data

(60) Provisional application No. 60/995,144, filed on Sep. 25, 2007, provisional application No. 60/988,950, filed on Nov. 19, 2007.

(51) Int. Cl.
*A01N 43/54* (2006.01)
*A61K 31/505* (2006.01)
*C07D 239/02* (2006.01)
(52) U.S. Cl. .................................. 514/273; 544/320
(58) Field of Classification Search .................. None
See application file for complete search history.

(56) References Cited

U.S. PATENT DOCUMENTS

| 2,748,125 | A | * | 5/1956 | Hofmann | 544/295 |
| 7,084,100 | B2 | | 8/2006 | Watson | |
| 2006/0089380 | A1 | | 4/2006 | Barnham et al. | |

FOREIGN PATENT DOCUMENTS

| CA | 2204582 | | 11/1997 |
| JP | EP0806422 | * | 12/1997 |

OTHER PUBLICATIONS

Andersen, J.K. "Oxidative stress in neurodegeneration: cause or consequence?" Nat Med 2004; 10(suppl):S18-S25.
Bakalbassis, E.G, et al. "Theoretical Calculation of Accurate Absolute and Relative Gas- and Liquid-Phase O-H Bond Dissociation Enthalpies of 2-Mono- and 2,6-Disubstituted Phenols, Using DFT/B3LY." J. Physical. Chem. A Oct. 16, 2003; 107(41):8594-8606.
Boscia, F., et al. "Protein oxidation and lens opacity in humans." Invest Ophthalmol Vis Sci. Aug. 2000;41(9):2461-5.
Chowers, I., et al. "The iron carrier transferrin is upregulated in retinas from patients with age-related macular degeneration." Invest Ophthalmol Vis Sci. May 2006;47(5):2135-40.
Ciarelli, L., et al. "Element concentrations and cataract: an experimental animal model." J Trace Elem Med Biol. Apr. 2001;14(4):205-9.
Cumurcu, T., et al. "Levels of zinc, iron, and copper in patients with pseudoexfoliative cataract." Eur J Ophthalmol. Jul.-Aug. 2006;16(4):548-53.
Dunaief, J.L. "Iron induced oxidative damage as a potential factor in age-related macular degeneration: the Cogan Lecture." Invest Ophthalmol Vis Sci. Nov. 2006;47(11):4660-4.

Gaeta, A., et al. "The crucial role of metal ions in neurodegeneration: the basis for a promising therapeutic strategy." Br J Pharmacol. Dec. 2005;146(8):1041-59.
Gal, S., et al. "Novel multifunctional neuroprotective iron chelator-monoamine oxidase inhibitor drugs for neurodegenerative diseases. In vivo selective brain monoamine oxidase inhibition and prevention of MPTP-induced striatal dopamine depletion." J Neurochem. Oct. 2005;95(1):79-88.
Garner, B., et al. "Distribution of ferritin and redox-active transition metals in normal and cataractous human lenses." Exp Eye Res. Dec. 2000;71(6):599-607.
Pratt, D.A., et al. "5-Pyrimidinols: Novel Chain-Breaking Antioxidants More Effective than Phenols." J Am Chem Soc 2001;123(19):4625-4626.
Gouras, G.K., et al. "Metal chelator decreases Alzheimer beta-amyloid plaques." Neuron. Jun. 2001;30(3):641-2.
Ikesugi, K., et al. "Role of the unfolded protein response (UPR) in cataract formation." Exp Eye Res. Sep. 2006;83(3):508-16. Epub Apr. 27, 2006.
Ismail, A.R., et al. "Hereditary hyperferritinemia cataract syndrome: ocular, genetic, and biochemical findings." Eur J Ophthalmol. Jan.-Feb. 2006;16(1):153-60.
Jinno, S., et al. "Synthesis and Structure-Activity Relationships of Phaffiaol and Related Antioxidants." Chem Pharm Bull. 1998;46(11):1688-1694.
Kador, P.F., et al. "Topical aldose reductase inhibitor formulations for effective lens drug delivery in a rat model for sugar cataracts." J Ocul Pharmacol Ther. Apr. 2007;23(2):116-23.
Kador, P.F., et al. "Anticataract activity of analogs of a sorbitol dehydrogenase inhibitor." J Ocul Pharmacol Ther. Aug. 2004;20(4):333-44.
Karslioglu, I., et al. "Radioprotective effects of melatonin on radiation-induced cataract." J Radiat Res (Tokyo). Jun. 2005;46(2):277-82.
Kaur, D., et al. "Ironing out Parkinson's disease: is therapeutic treatment with iron chelators a real possibility?" Aging Cell. Oct. 2002;1(1):17-21.
Lengyel, I., et al. "High concentration of zinc in sub-retinal pigment epithelial deposits." Exp Eye Res. Apr. 2007;84(4):772-80. Epub Jan. 9, 2007.
Mandel, S.A., et al. "Multifunctional activities of green tea catechins in neuroprotection. Modulation of cell survival genes, iron-dependent oxidative stress and PKC signaling pathway." Neurosignals. 2005;14(1-2):46-60.
Mandel, S., et al. "Green tea catechins as brain-permeable, natural iron chelators-antioxidants for the treatment of neurodegenerative disorders." Mol Nutr Food Res. Feb. 2006;50(2):229-34.
Popescu, C., et al. "The mechanism of cataract formation in persons with beta-thalassemia." Oftalmologia. 1998;45(4):10-3 [Abstract].
Roetto, A., et al. "Pathogenesis of hyperferritinemia cataract syndrome." Blood Cells Mol Dis. Nov.-Dec. 2002;29(3):532-5.

(Continued)

*Primary Examiner* — Jeffrey Murray
(74) *Attorney, Agent, or Firm* — Dann, Dorfman, Herrell & Skillman; Robert C. Netter, Jr.

(57) ABSTRACT

Compositions comprising multifunctional agents and methods of use thereof are provided. Particularly, a series of analogs of 1-N, N'-dimethylsulfamoyl-4-(2-pyrimidyl)piperazine are provided which are useful for treating and/or preventing cataract, macular degeneration, neurodegenerative disorders, and/or injury or symptoms associated with radiation exposure.

10 Claims, 18 Drawing Sheets

OTHER PUBLICATIONS

Figure 1:
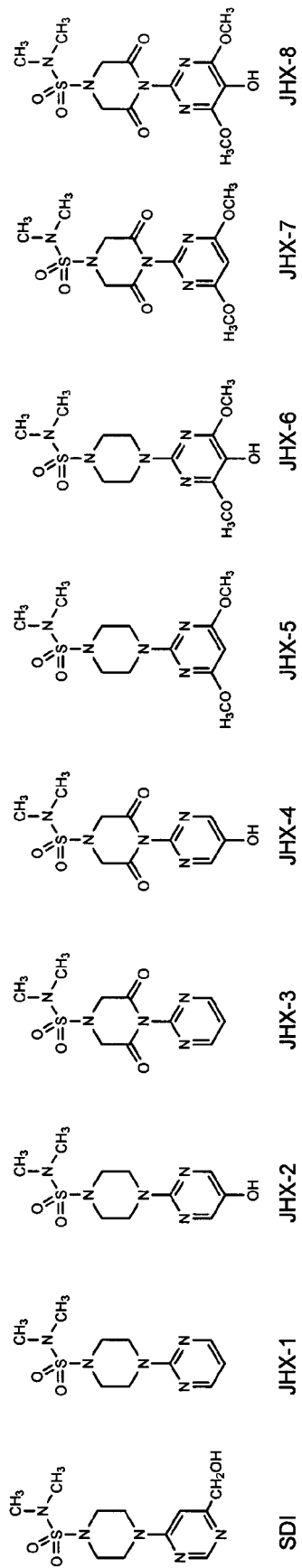

Shalini, V.K, et al. "Oxidative damage to the eye lens caused by cigarette smoke and fuel smoke condensates." Indian J Biochem Biophys. Aug. 1994;31(4):261-6.

Smith, D.G., et al. "The redox chemistry of the Alzheimer's disease amyloid beta peptide." Biochim Biophys Acta. Aug. 2007;1768(8):1976-90. Epub Feb. 9, 2007.

Storr, T., et al. "Synthesis, characterization, and metal coordinating ability of multifunctional carbohydrate-containing compounds for Alzheimer's therapy." J Am Chem Soc. Jun. 13, 2007;129(23):7453-63. Epub May 19, 2007.

Truscott, R.J. "Age-related nuclear cataract-oxidation is the key." Exp Eye Res. May 2005;80(5):709-25.

Vanita, V., et al. "Sutural cataract associated with a mutation in the ferritin light chain gene (FTL) in a family of Indian origin." Mol Vis. Feb. 2006;12:93-9.

Yao, J.K., et al. "Determination of multiple redox-active compounds by high-performance liquid chromatography with coulometric multi-electrode array system." J Chromatogr B Analyt Technol Biomed Life Sci. Oct. 15, 2004;810(1):93-100.

Zaidi, S.A.A., et al. "Transition Metal Complexes of 2-(N-Succinimidyl)Pyrimidine." Inorg. Metal-Organ. Chem. 1993;23(9):1571-84.

Zheng, H., et al. "Novel multifunctional neuroprotective iron chelator-monoamine oxidase inhibitor drugs for neurodegenerative diseases: in vitro studies on antioxidant activity, prevention of lipid peroxide formation and monoamine oxidase inhibition." J Neurochem. Oct. 2005;95(1):68-78.

Zheng, H., et al. "Design, synthesis, and evaluation of novel bifunctional iron-chelators as potential agents for neuroprotection in Alzheimer's, Parkinson's, and other neurodegenerative diseases." Bioorg Med Chem. Feb. 1, 2005;13(3):773-83.

Randazzo, J. "Development of Multi-functional Anti-oxidants." PowerPoint Presentation Nov. 17, 2006. Presented at the Pharmaceutical Sciences Graduate Program at the University of Nebraska Medical Center, Omaha, NE.

* cited by examiner

MULTIFUNCTIONAL ANTIOXIDANTS AND METHODS OF USE THEREOF

This application claims priority under 35 U.S.C. §119(e) to U.S. Provisional Patent Application No. 60/995,144, filed on Sep. 25, 2007 and to U.S. Provisional Patent Application No. 60/988,950, filed on Nov. 19, 2007. The foregoing applications are incorporated by reference herein.

This invention was made with government support under Grant No. 1R21 EY016460-01 awarded by the National Institutes of Health. The government has certain rights in the invention.

FIELD OF THE INVENTION

This invention relates generally to the fields of cataracts, macular degeneration, neurodegenerative disorders, radiation exposure injury and methods of treatment thereof. Specifically, the invention provides orally active multifunctional antioxidants with chelation activity and/or free radical scavenging activity.

BACKGROUND OF THE INVENTION

Neurodegenerative disorders such as Alzheimer's disease (AD), Parkinson's disease (PD), Lewy Body disease (LBD), amyotrophic lateral sclerosis (ALS) and prion diseases (PrD), while pathologically different, can undergo similar abnormal metallochemical reactions between proteins and the redox-active metal ions copper or iron. These reactions damage cellular components and result in abnormal protein aggregation through the generation of reactive oxygen species (ROS) which include free radicals such as superoxide anion and hydroxyl radical and other molecular species such as hydrogen peroxide and peroxynitrite (Droge and Schipper (2007) Aging Cell, 6:361-70; Bush and Goldstein (2001) Novartis Found. Symp., 235:26-43; Moreira et al. (2005) J. Neural. Transm., 112:921-32; Butterfield and Kanski (2001) Mech. Ageing Dev., 122:945-62; Wisniewski and Sigurdsson (2007) Febs J., 274:3784-98).

Cellular ROS are generated as a side product in mitochondria because of incomplete metabolic reduction of molecular oxygen ($O_2$) to water. Common ROS include the superoxide anion ($O_2^-$), the hydroxyl radical (OH.), singlet oxygen ($^1O_2$), and hydrogen peroxide ($H_2O_2$). Superoxide anions are continuously formed in the mitochondria as molecular oxygen ($O_2$) acquires an additional electron. Hydroxyl radicals are the most reactive and damaging generated ROS. They are predominantly formed by a Fenton reaction between transitions metals (usually iron(II) or copper(I)) and hydrogen peroxide; however, it can also be formed through the Haber-Weiss reaction of superoxide anion and hydrogen peroxide. Although these metals are oxidized in this process, they are returned to their "active" (reduced) state through a process of 'redox cycling' with vitamin C or other cellular reductants. Hydrogen peroxide, produced in vivo through several reactions, can either be converted to the highly reactive and damaging hydroxyl radicals or converted to water. It is formed by the reduction of superoxide radical by superoxide dismutase and reduced to water by either catalase or glutathione peroxidase. Hydrogen peroxide can also form singlet oxygen. While not a free radical, singlet oxygen is highly reactive because it can serve as a catalyst for free radical formation by transferring its energy to other molecules.

ROS damages cellular components by oxidizing proteins, lipid bilayers, and DNA. This can result in alterations of protein conformations and enzyme activities. With polyunsaturated fatty acids, ROS can generate lipid peroxides which subsequently can oxidize adjacent unsaturated fatty acids in a chain reaction event that leads to the disruption of plasma membranes and membranes of cellular organelle components, such as the mitochondria. Characteristic break-down products of lipid oxidation include 4-hydroxynonenal (4-HNE) and malondialdehyde (MDA). Oxidation of DNA results in strand breaks, DNA-protein cross-linking, and base modifications that can lead to mutations impacting DNA replication. Cells possess a variety of enzymatic and non-enzymatic antioxidant systems to protect against ROS damage. However, several of these protective enzymes, such as cytosolic copper-zinc superoxide dismutase (CuZnSOD) and mitochondrial manganese superoxide dismutase (MnSOD), contain metals. As a result, cells must maintain a delicate balance between free and bound pro-oxidant versus antioxidant metal ions that are critical to cellular homeostasis. The aging brain has a progressive imbalance between antioxidant defenses and intracellular concentrations of ROS.

Oxidative stress results from an imbalance between biochemical processes leading to the production of ROS and those responsible for the removal of ROS, the so-called antioxidant cascade. Oxidative stress increases with age and prolonged tissue exposure to oxidative stress results in cellular damage that eventually leads to cell death. Neural tissues of the brain are especially susceptible to ROS and oxygen free radical activity has been observed in the brain hippocampus, substantia nigra, caudate putamen and in the spinal fluid. The increased susceptibility of the neural tissues is due to their higher metabolic rates, high compositions of peroxidation susceptible fatty acids, high intracellular concentrations of transition metals capable of catalyzing Fenton reactions, low levels of antioxidants, and a reduced capability of tissue regeneration. In addition to the mitochondrial generation of ROS, neural tissues possess brain-specific oxidases such as monoamine oxidase that also generate hydrogen peroxide. ROS also results from neuroinflammatory responses induced by reactive microglia, macrophages and proinflammatory T-cells.

Many consider oxidative damage to be a hallmark of neurodegenerative disorders and the relationship between ROS and neurodegenerative disorders has been extensively reviewed (Floyd, R. A. (1999) Proc. Soc. Exper. Biol. Med., 222:236-45; Doraiswamy and Finefrock (2004) Lancet Neurology, 3:431-4; Reynolds et al. (2007) Int. Rev. Neurobiol., 82:297-325; Andersen, J. K. (2004) Nature Med., 10:S18-25; Sayre et al. (2005) Ann. Ist. Super Sanita, 41:143-64; Casadesus et al. (2004) J. Alzheimers Dis., 6:165-9; Gaggelli et al. (2006) Chem. Rev., 106:1995-2044). With normal ageing, the brain accumulates metals ions such iron (Fe), copper (Cu), and zinc (Zn) and a major focus of studies on the generation of neurodegenerative ROS has been the involvement of the redox-reactive metals.

Metal-protein associations with Cu(II), Fe(III), or Mn(II) can also lead to protein aggregation. Cu, Zn and Fe accumulate in β-amyloid (Aβ) deposits in the brains of patients with AD (Lovell et al. (1998) J. Neurol. Sci., 158:47-52). Both the amyloid precursor protein and Aβ bind and reduce Cu. Cu binding to Aβ promotes the aggregation of Aβ into metal-enriched precipitates (plaques) and the abnormal combination of Aβ with Cu or Fe induces the production of hydrogen peroxide (Smith et al. (2007) Biochim. Biophys. Acta, 1768:1976-90; Bush, A. I. (2002) Neurobiol. Aging, 23:1031-8). Addition of Zn to synthetic Aβ induces protease resistant aggregation and precipitation of the synthetic Aβ (Barnham et al. (2006) Trends Biochem. Sci., 31:465-72; Huang et al. (1997) J. Biol. Chem., 272:26464-70). Cu can also bind to α-synuclein, a protein observed to aggregate in Lewy Bodies of PD. While its present role in neurodegeneration is undefined and controversial, copper chelators appear to prevent its aggregation (Brown, D. R. (2007) FEBS J., 274:3766-74). Regardless, metal chelation has been proposed for the treatment of neurodegenerative disorders such as Parkinson's Disease and Alzheimer's (Gaeta et al. (2006) Br. J. Pharmacol., 146:1041-1059; Kaur et al. (2002) Aging Cell 1:17-21; Gouras et al. (2001) 30:641-642).

While the relationship(s) between neurodegeneration, ROS and redox-reactive metal ions have not been clearly defined, studies suggest that targeting oxidative pathways may be therapeutic (Smith et al. (2007) Biochim. Biophys. Acta, 1768:1976-90). A wide variety of antioxidants have been examined to reduce ROS. These range from natural products with antioxidant properties such as aged garlic extract, curcumin, melatonin, resveratrol, *Ginkgo biloba* extract, green tea, vitamin C, L-caritine, vitamin E, and cannabinoids to derivatives of lipoic acid, analogs of Coenzyme Q (MitoQ), and the "thiol-delivering" glutathione-mimics such as tricyclodecan-9-yl-xanthogenate (Frank and Gupta (2005) Ann. Clin. Psych., 17:269-86; Garcia-Arencibia et al. (2007) Brain Res., 1134:162-70; Bolognesi et al. (2006) Mini Rev. Med. Chem., 6:1269-74; Binienda et al. (2005) Annal. NY Acad. Sci., 1053:174-82; Tauskela et al. (2007) Idrugs, 10:399-412; Perluigi et al. (2006) Neuroscience, 138:1161-70).

Chelation of redox-active metals is another promising approach to reduce the generation of ROS. A number of structurally diverse chelators have been evaluated (desferrioxamine (DFO), clioquinol, JKL 169, D-penicillamine, DP-109, VK-28, epicatechin-3-gallate (ECG), epigallocatechin-3-gallate (EGCG), epicatechin (EC), epigallocatechin (ECG), H2GL1, H2GL2, M-30); however, the hydrophobic natures of many of these chelators hinder their ability cross the BBB. Desferrioxamine, an iron specific chelator with high affinity for Cu, Zn and Al, has been reported to decrease the progression of Alzheimer's disease (McLachlan et al. (1991) Lancet, 337:1304-8; McLachlan et al. (1993) Ther. Drug Monit., 15:602-7). However, this compound is not orally active and does not significantly cross the BBB (Cuajungco and Lees (1998) Brain Res., 799:97-107; Finefrock et al. (2003) J. Am. Geriatr. Soc., 51:1143-8). Clioquinol is an orally active antibiotic that also chelates metals. Through chelation, it reduces Cu uptake and counteracts Cu efflux activities of the amyloid precursor protein of AD (Treiber et al. (2004) J. Biol. Chem., 279:51958-64), disaggregates the metal ion-induced aggregates of Aβ(1-40), and retards fibril growth through Zn(II)-clioquinol complex formation (Raman et al. (2005) J. Biol. Chem., 280:16157-62). Its efficacy has been demonstrated in vitro, in vivo in animal models, and in several small clinical trials where statistically significant results were seen in the more severely affected subgroups of AD patients (Jenagaratnam and McShane (2006) Cochrane Database Of Systematic Reviews; Smith et al. (2007) Biochim. Biophys. Acta, 1768:1976-90; Crouch et al. (2006) Drug News & Perspect., 19:469-74; Rose and Gawel (1984) Acta Neuro. Scand. Supp., 100:137-45). JKL169 is a 14-membered saturated tetramine that when injected into rats has been reported to demonstrate activity similar to clioquinol in reducing Cu levels in brain cortex and maintaining normal Cu levels in the blood, CSF and corpus callossum (Moret et al. (2006) Bioorg. Med. Chem. Lett., 16:3298-301). DP109 is a lipophilic chelator that reduced the levels of aggregated insoluble Aβ and conversely increased soluble forms in transgenic mice (Lee et al. (2004) Neurobiol. Aging, 25:1315-21). D-penicillamine, which also chelates copper, has been reported to delay the onset of prion disease in mice infected with scrapie (Sigurdsson et al. (2003) J. Biol. Chem., 278: 46199-202).

Recent reports have also focused on the potential treatment of neurodegenerative diseases by combining chelation with antioxidant/neuroprotective therapy. For example, green tea extract (catechins) and its major component, EGCG, possess divalent metal chelating, antioxidant, and anti-inflammatory activities (Mandel et al. (2006) Mol. Nutr. Food Res., 50:229-34). In addition, catechins may modulate signal transduction pathways, cell survival/death genes and mitochondrial function (Mandel et al. (2005) Neurosignals, 14:46-60). Both have been reported to prevent striatal dopamine depletion in mice as well as substantia nigra dopaminergic neuron loss induced by the PD-inducing neurotoxin N-methyl-4-phenyl-1,2,3,6-tetrahydropyridine (MPTP) (Levites et al. (2001) J. Neurochem., 78:1073-82). Similarly neuroprotective affects have been observed with in vitro studies with extracts from anthocyanin rich Vaccinium species (Yao and Vieira (2007) Neurotoxicology, 28:93-100). Clinical efficacy of neither green tea constituents nor other flavonoids has been established. Several novel antioxidant-iron chelators bearing 8-hydroxyquinoline moiety (VK-28 and M30) have also been synthesized and evaluated for their ability to chelate iron and possess neuroprotective activity (Zheng et al. (2005) Bioorg. Med. Chem., 13:773-83). In vitro, these compounds were able to chelate Fe, scavenge hydroxyl radicals, and inhibit monoamine oxidase (MAO) (Zheng et al. (2005) J. Neurochem., 95:68-78). In vivo, both inhibited MAO with M30 demonstrating brain selective (striatum, hippocampus and cerebellum) irreversible MAO-A and -B inhibition in mice (Gal et al. (2005) J. Neurochem., 95:79-88). The synthesis of two multifunctional carbohydrate-containing compounds N,N'-bis[(5-β-D-glucopyranosyloxy-2-hydroxy)-benzyl]-N, N'-dimethylethane-1,2-diamine (H2GL1) and its t-butyl-analog (H2GL2) have recently been reported (Storr et al. (2007) J. Am. Chem. Soc., 129:7453-7463). Initial in vitro studies suggest that both of these water soluble, carbohydrate-containing compounds have significant antioxidant capacity and moderate affinity for Cu(II) and Zn(II). While in vivo studies have not been reported, sugar moieties have been added to these molecules in anticipation that these water soluble compounds will utilize GLUT transporters to cross the BBB.

ROS and the Fenton reaction as well as the presence of metals such as Fe and Cu have also been implicated in cataracts and macular degeneration. Indeed, it has been well established that cataract and macular degeneration are initiated by oxidation and oxidative stress. With regard to cataracts, it has also been shown that Fe and Cu levels in serum are increased in patients with psuedoexofoliative cataracts (Cumurcu et al. (2006) 16:548-52) and cataracts has also been associated with hyperferritinemia (Ismail et al. (2006) 16:153-160; Vanita et al. (2006) Mol. Vis., 12:93-99; Roetto et al. (2002) 29:532-535). It has also been determined that lens levels of Cu in diabetic patients is significantly higher compared to non-diabetic patients and that tobacco smoke increases lens Fe levels (Dawczynski et al. (2002) Biol. Trace Elem. Res., 15-24; Avunduk et al. (1997) Exp. Eye Res., 65:417-423). With regard to macular degeneration, iron induced oxidative damage has been identified as a potential factor in macular degeneration as Fe and Zn levels and the iron carrier transferrin have been shown to be increased in eyes with macular degeneration (Chowers et al. (2006) Invest. Opthalmol. Vis. Sci., 47:2135-2140; Dunaief, J. L. (2006) Invest. Opthalmol. Vis. Sci., 47:4660-4664; Lengyel et al. (2007) 84:772-780). Macular degeneration has also been observed in a patient with aceruloplasminemia, a disease associated with retinal iron overload (Dunaief et al. (2005) Opthalmol., 112:1062-1065). Additionally, it has been noted that maculas affected by macular degeneration contain increased chelatable iron in the retinal pigment epithelium and Bruch's membrane (Hahn et al. (2003) 121:1099-1105).

SUMMARY OF THE INVENTION

In accordance with the instant invention, multifunctional antioxidants with chelation activity and/or free radical scavenging activity are provided. Compositions comprising at least one of the compounds of the instant invention and at least one pharmaceutically acceptable carrier are also provided.

In accordance with another aspect of the instant invention, methods of treating and/or preventing cataract, macular degeneration, a neurodegenerative disorder, and/or injury or symptoms associated with radiation exposure are provided wherein a therapeutically effective amount of the compositions of the instant invention are administered to a patient in need of such treatment.

BRIEF DESCRIPTIONS OF THE DRAWING

FIG. 1 provides chemical structures of analogs of 1-N,N'-dimethylsulfamoyl-4-(2-pyrimidyl)piperazine (JHX-1).

Figure 2:
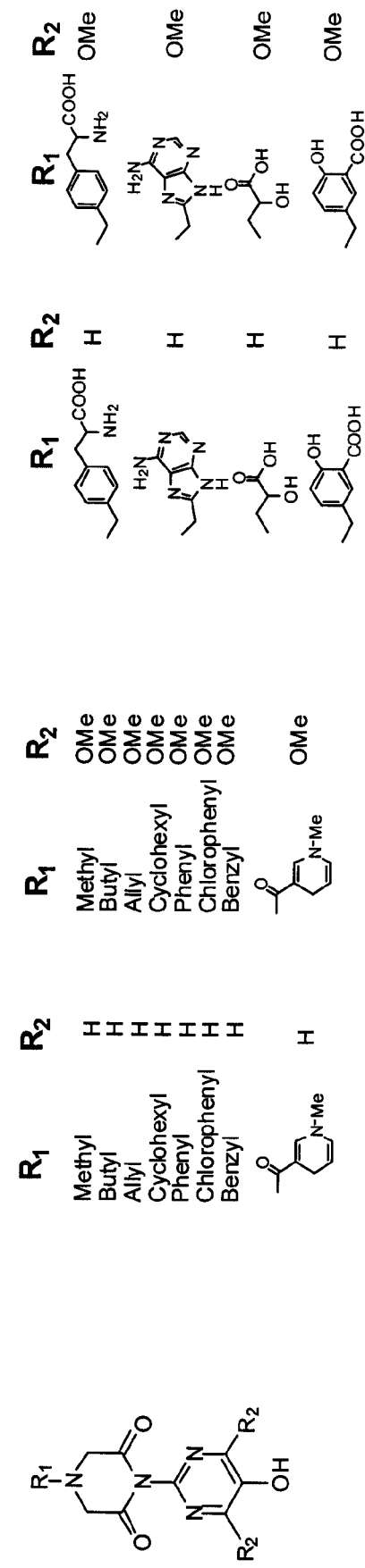

FIG. 2 provides chemical structures of additional analogs of 1-N,N'-dimethylsulfamoyl-4-(2-pyrimidyl)piperazine (JHX-1).

Figure 3:
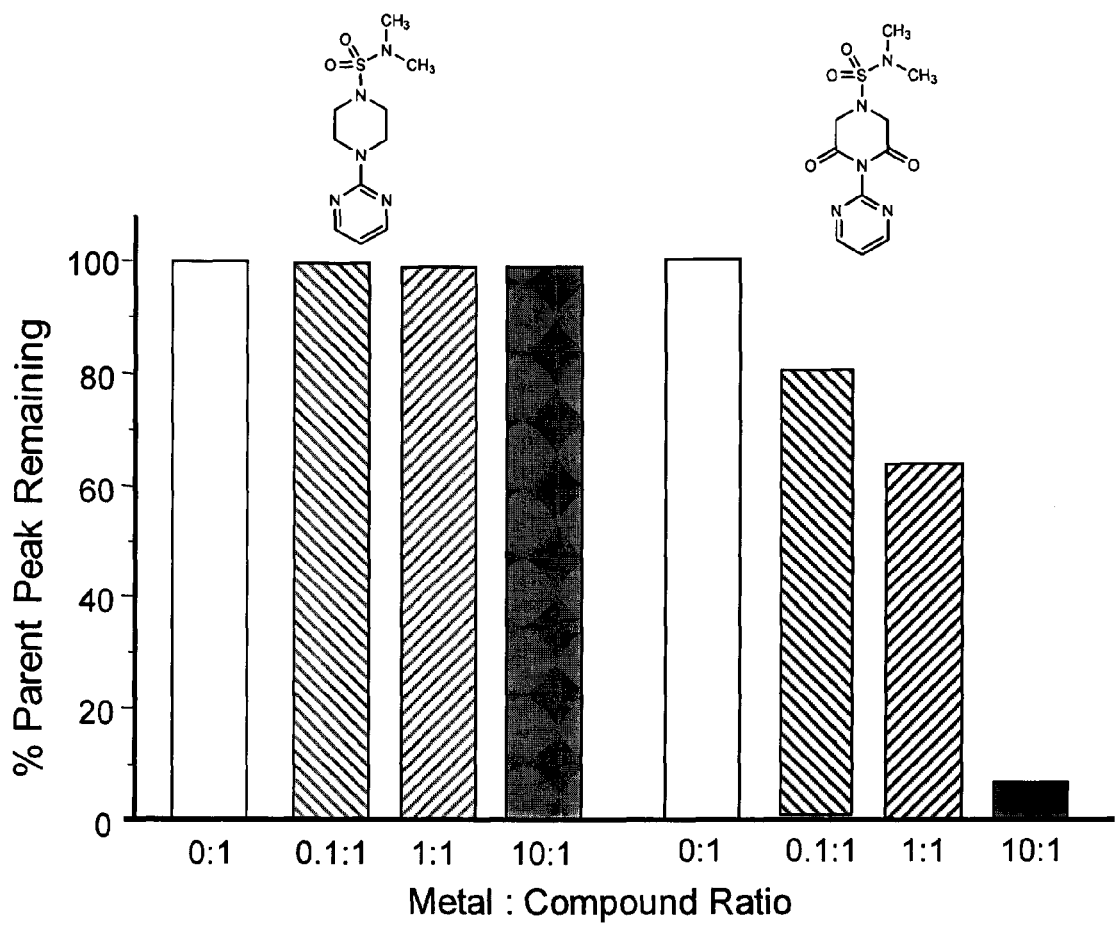

FIG. 3 is a graph depicting the percentage of parent peak remaining in $Fe^{2+}$ solutions for JHX-1 (left) and JHX-3 (right).

Figure 4A:
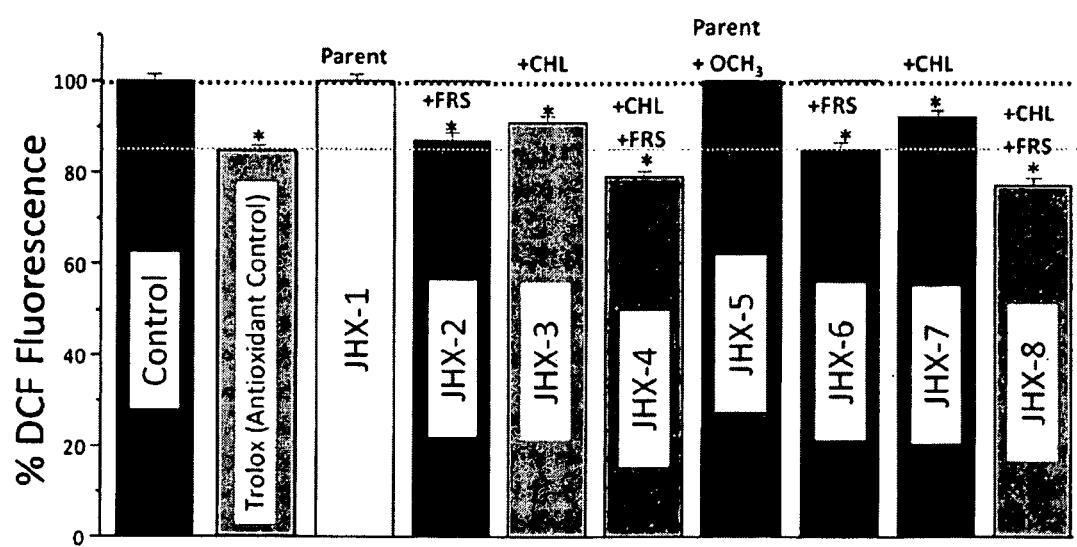
Figure 4B:
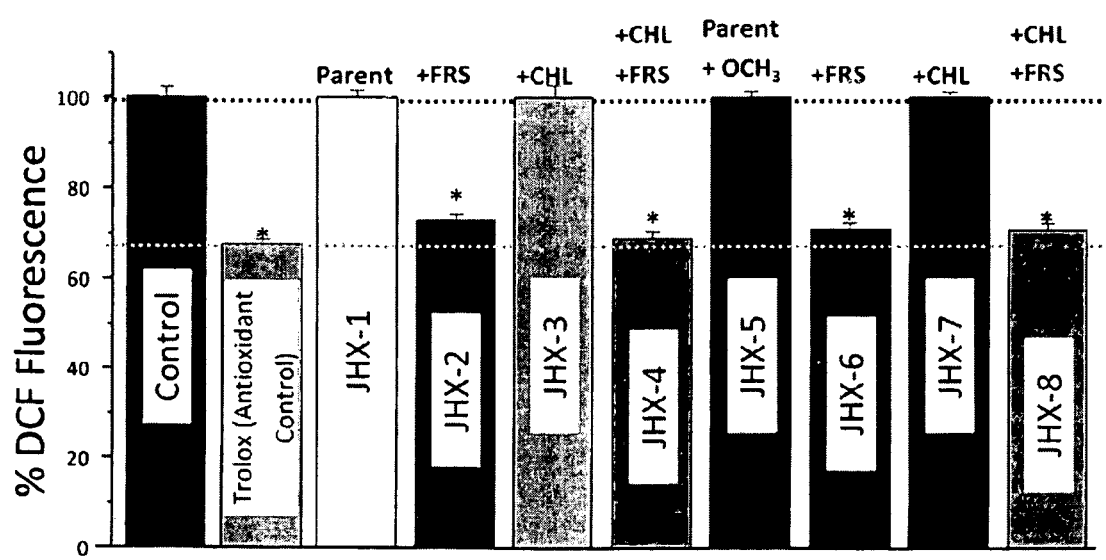

FIG. 4A is a graph of the reduction in reactive oxygen species (ROS) stain resulting from 24 hour incubation with the Fenton reaction. FIG. 4B is a graph of the reduction in ROS stain initiated by 24 hour incubation with homocysteine. Mean±standard deviation (SD). * $p<0.05$ compared to control.

Figure 5A:
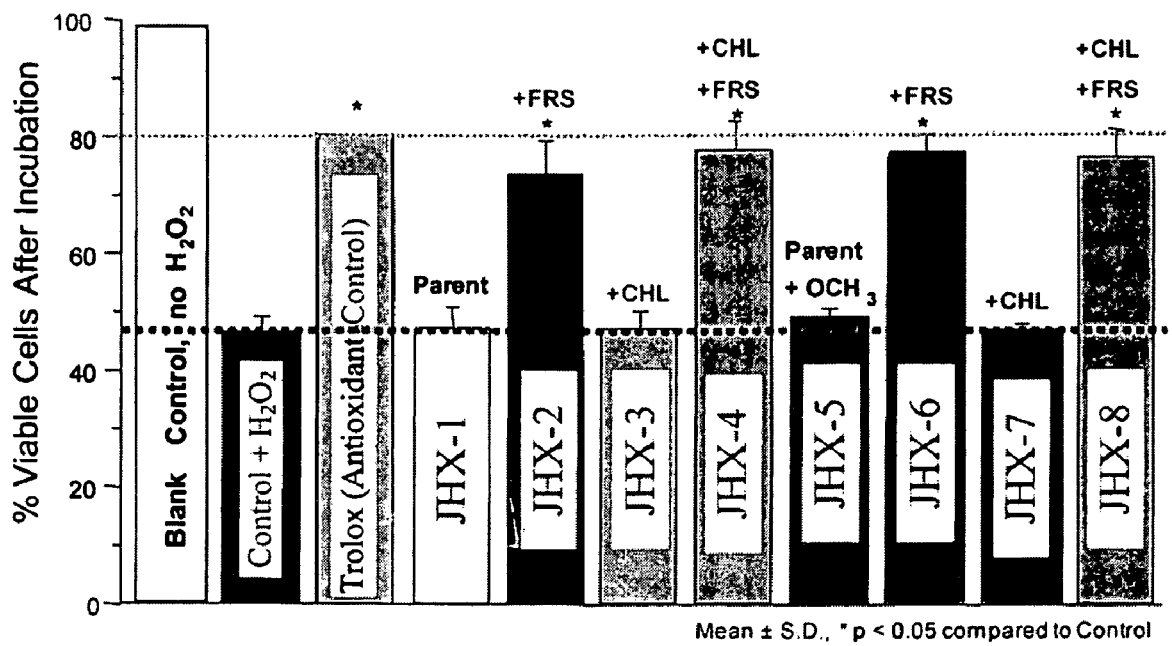
Figure 5B:
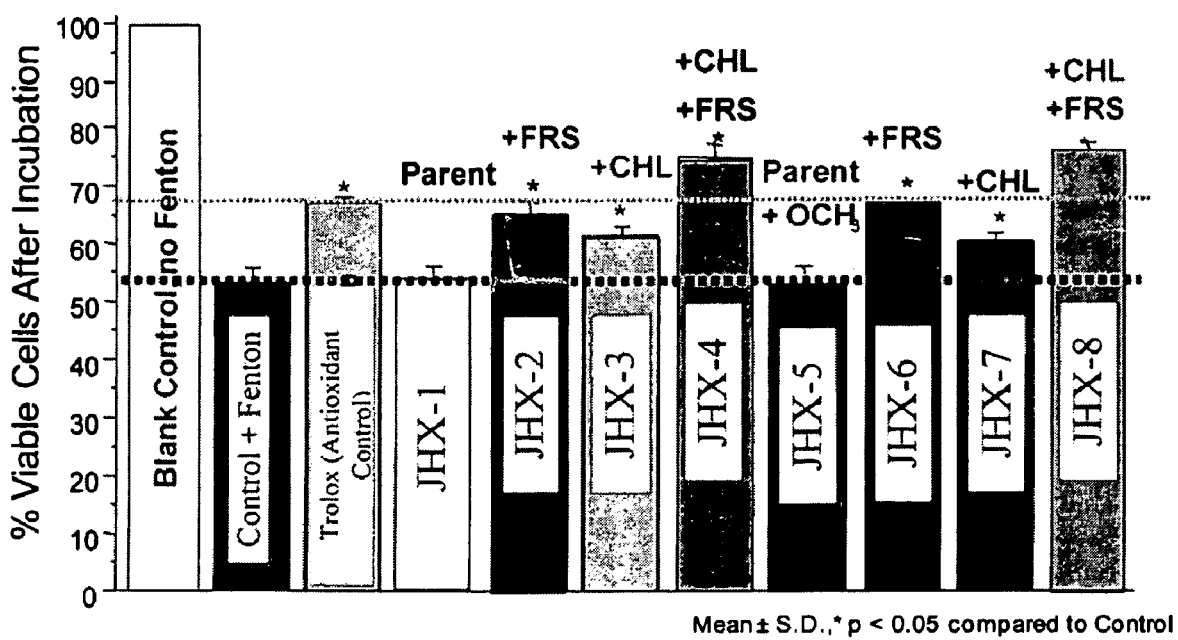

FIG. 5A is a graph of the percentage of viable human lens epithelial cells after culturing for two hours with 1 mM hydrogen peroxide and the indicated compounds. FIG. 5B is a graph of the percentage of viable human lens epithelial cells after culturing for to two hours with 1 mM Fenton reagents and the indicated compounds.

Figure 6:
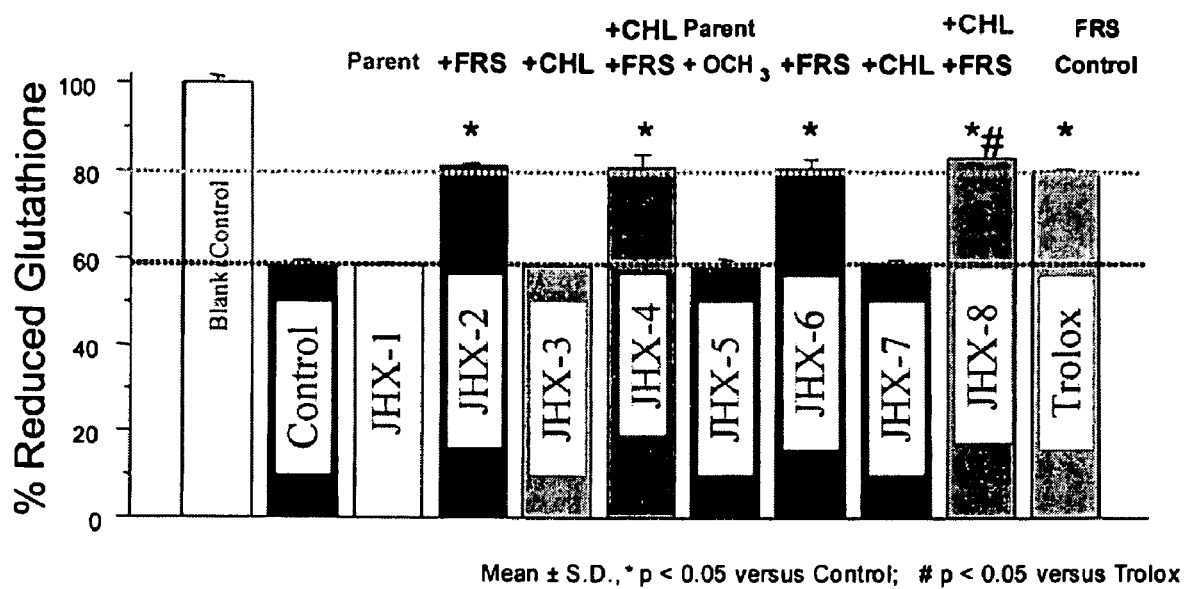

FIG. 6 provides a graph of the reduced glutathione with human lens epithelial cells incubated with 1 mM hydrogen peroxide and the indicated compounds for two hours.

Figure 7:
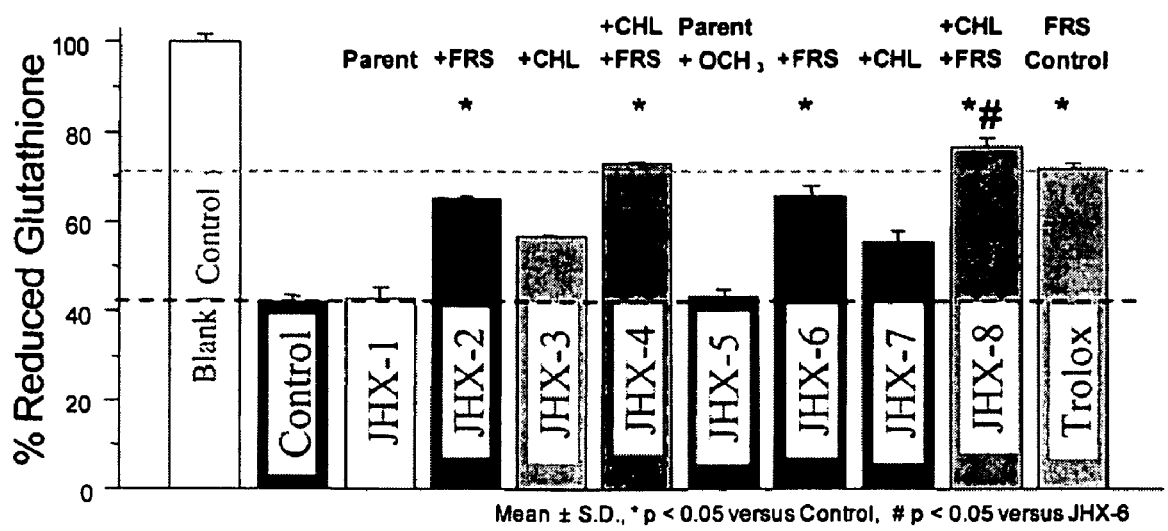

FIG. 7 provides a graph of the reduced glutathione with human lens epithelial cells incubated with 1 mM Fenton reagents and the indicated compounds for two hours.

Figure 8A:
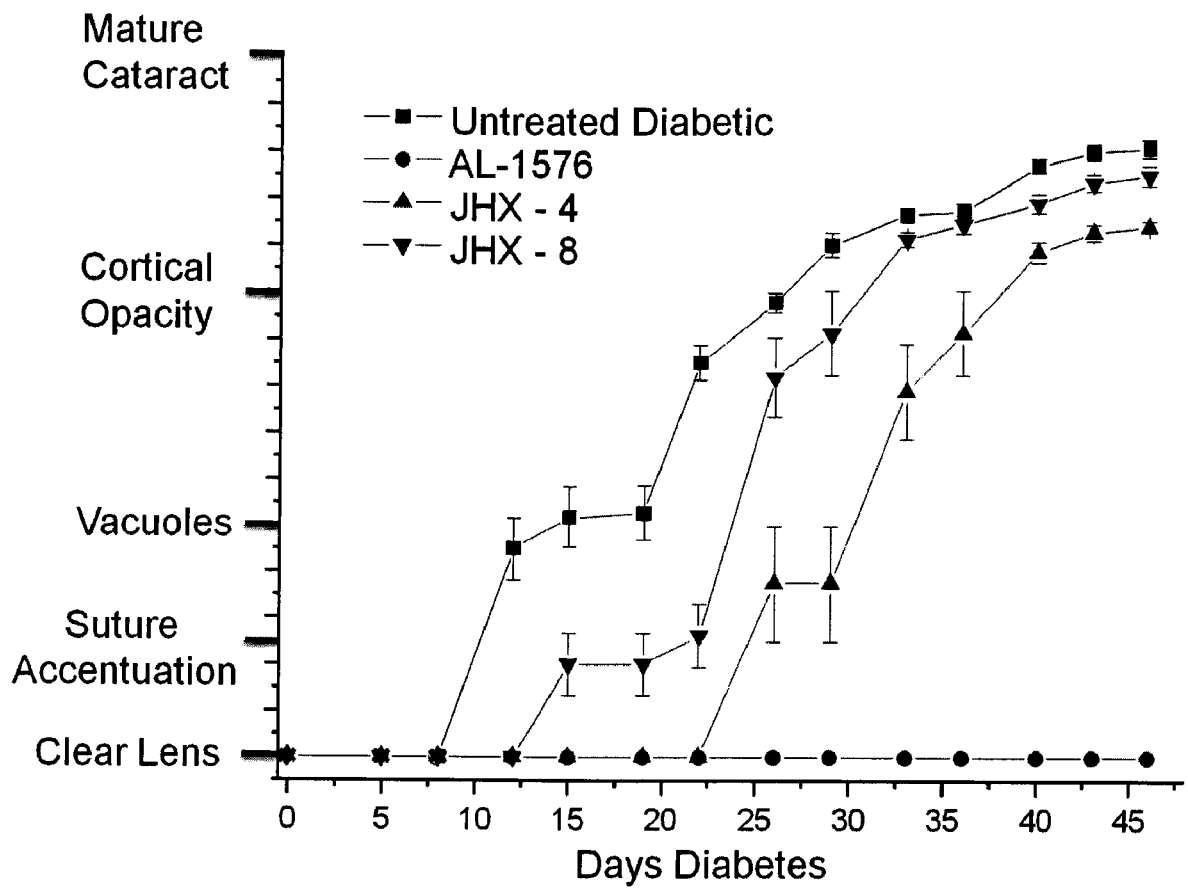
Figure 8B:
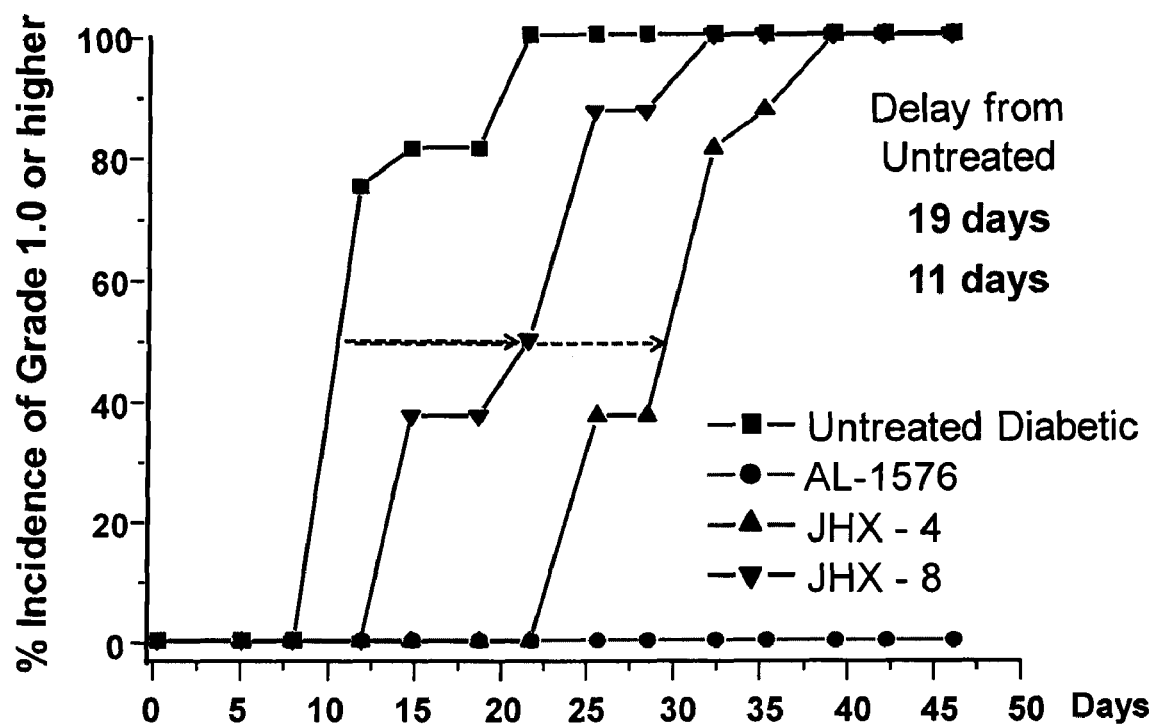
Figure 8C:
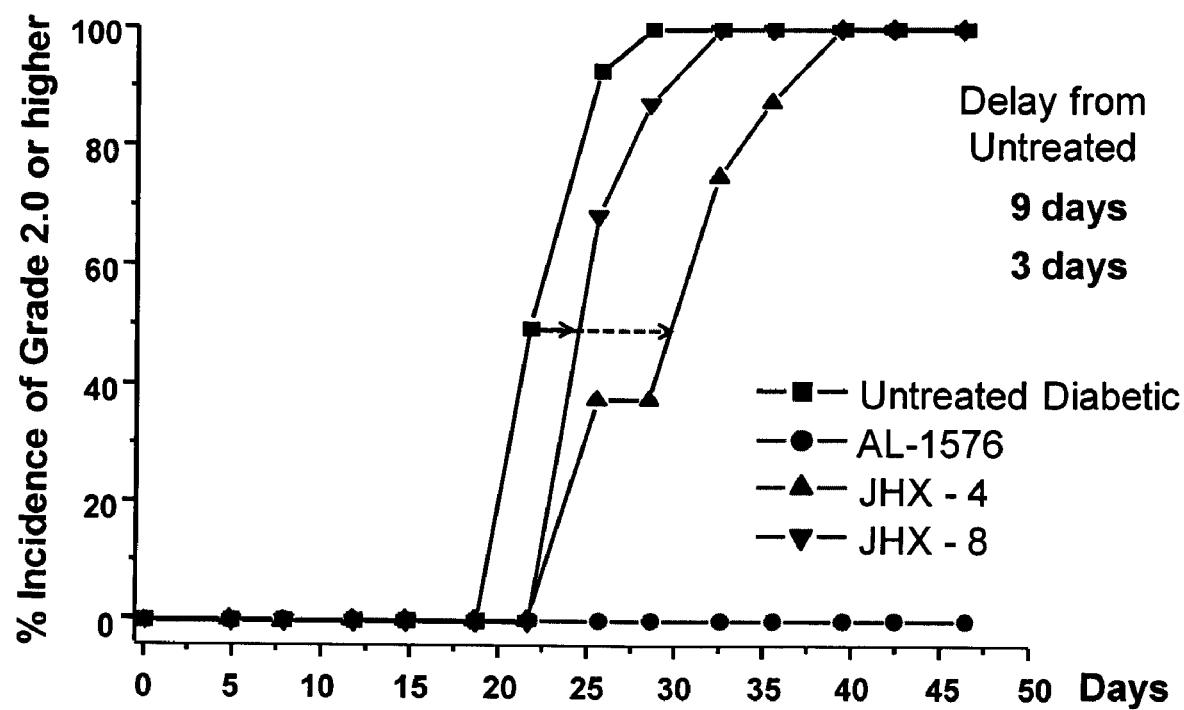

FIG. 8A is a graph of the development of cataract in mice treated with the indicated compound. FIGS. 8B and 8C summarize the increasing incidence of vacuole formation and the incidence of cortical opacities, respectively.

Figure 9:
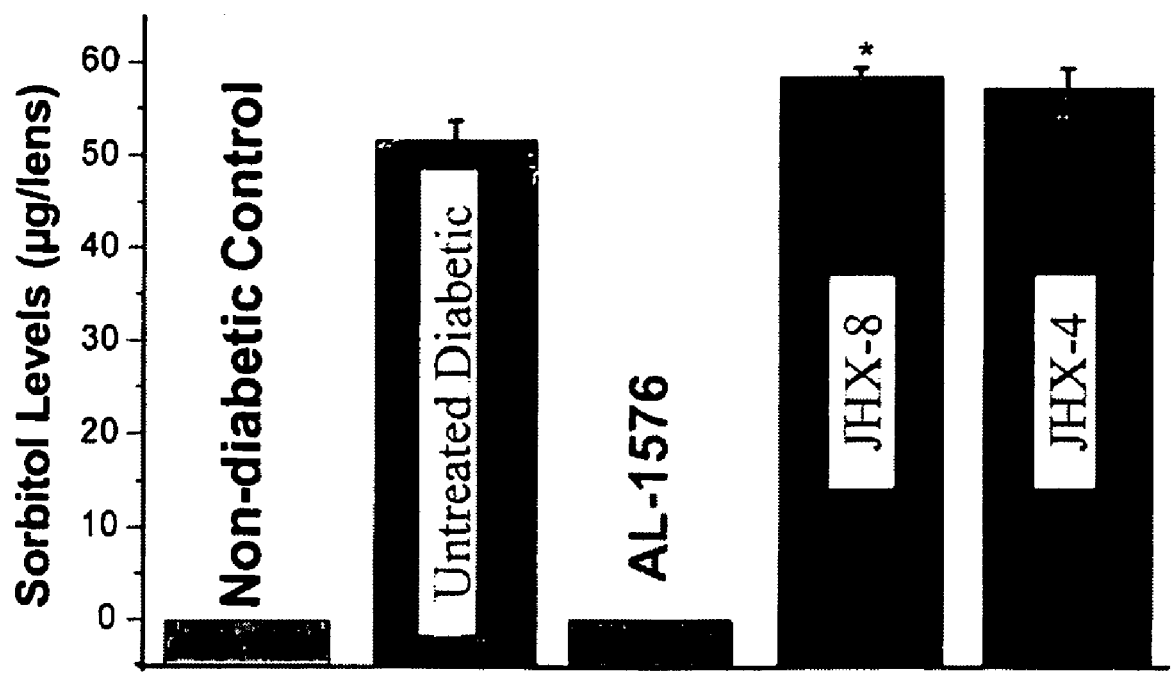

FIG. 9 provides a graph of lens sorbitol levels in mice treated with the indicated compound. Mean±SD. * $p<0.05$.

Figure 10A:
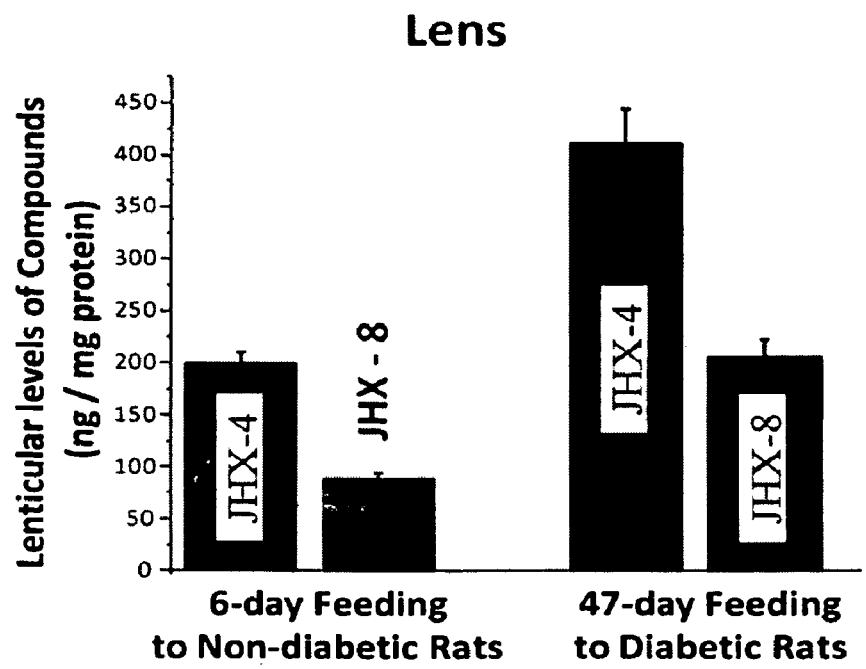
Figure 10B:
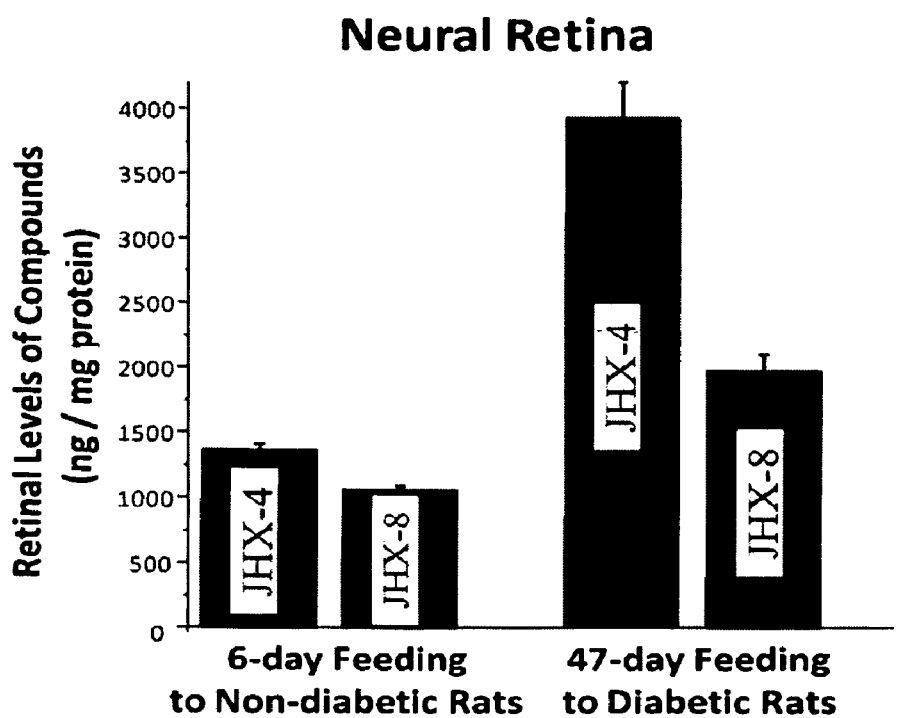

FIGS. 10A and 10B are graphs of the lens and neural retinal levels, respectively, of JHX-4 or JHX-8 in normal and diabetic rats. Mean±SD.

Figure 11:
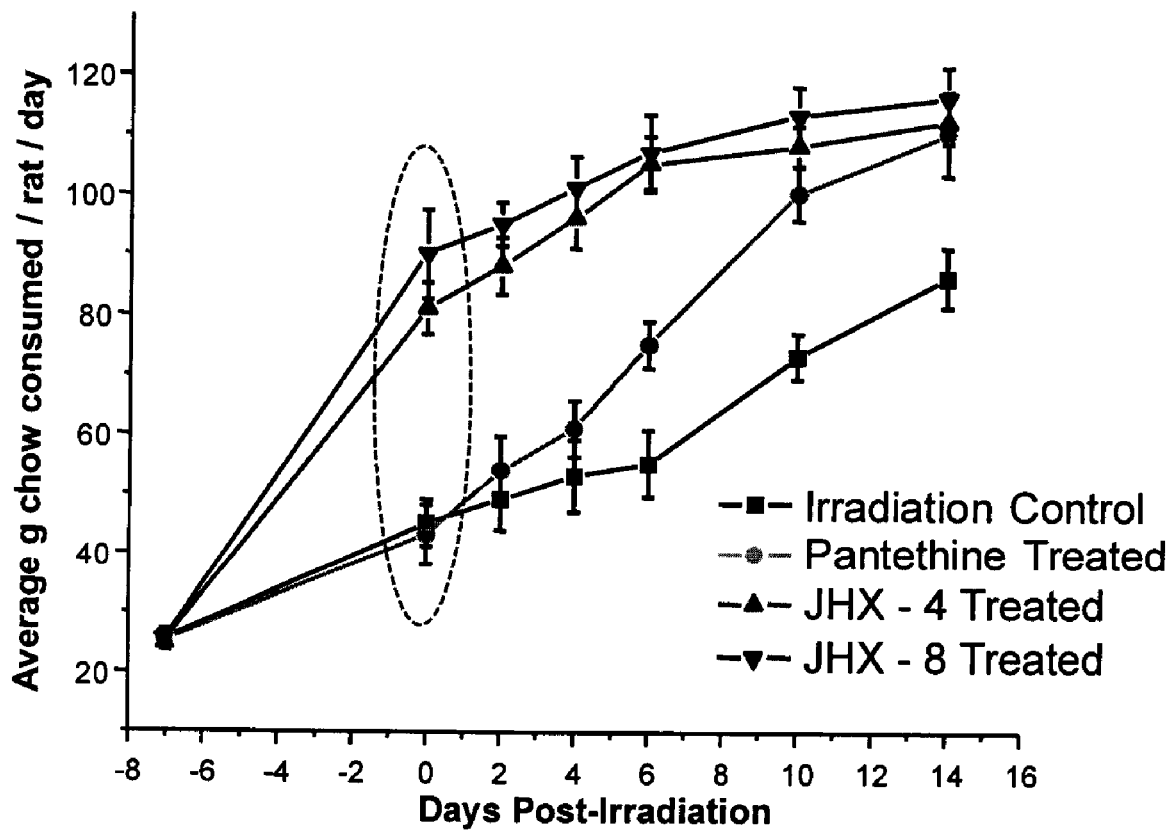

FIG. 11 is a graph depicting the consumption of chow in rats pre and post irradiation. All rats received Nutra-Gel (BioServ) starting at day 0. Dashed oval area depicts difference in consumption at day 0. Mean±SD.

Figure 12:
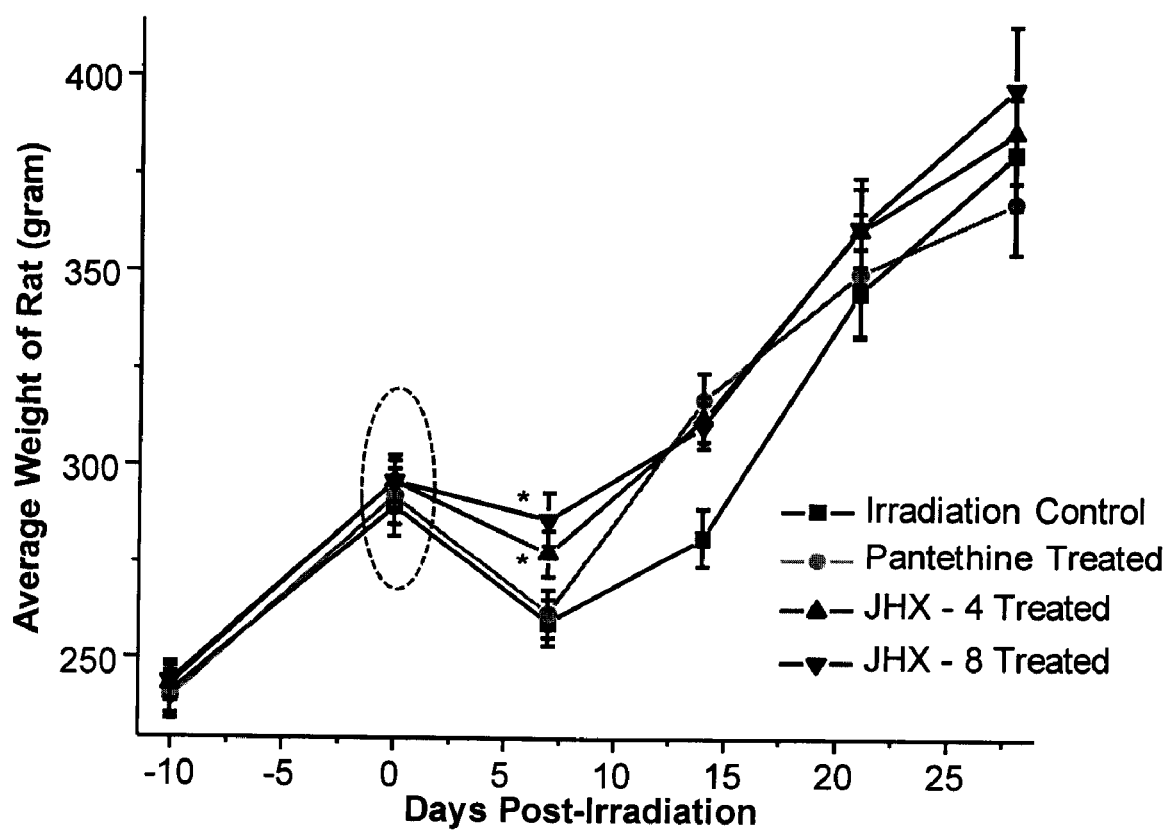

FIG. 12 is a graph depicting the weight gain of rats pre and post irradiation. Dashed oval area depicts weight on the day of irradiation. Mean±SD.

Figure 13:
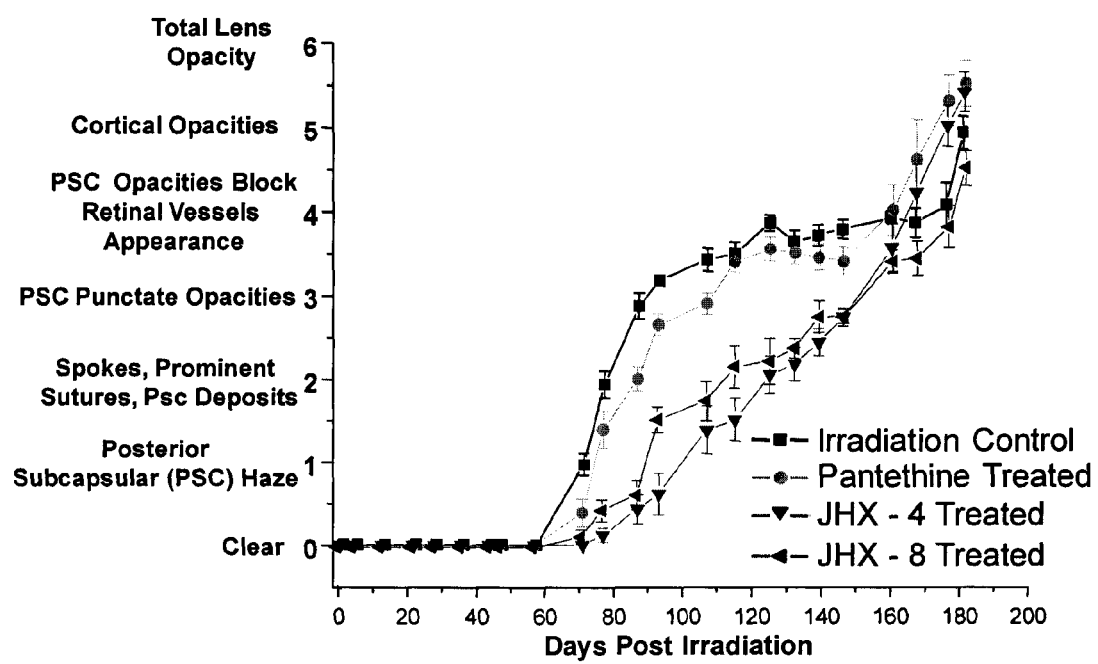

FIG. 13 is a graph of the progression of lens opacities in whole head irradiated mice.

Figure 14A:
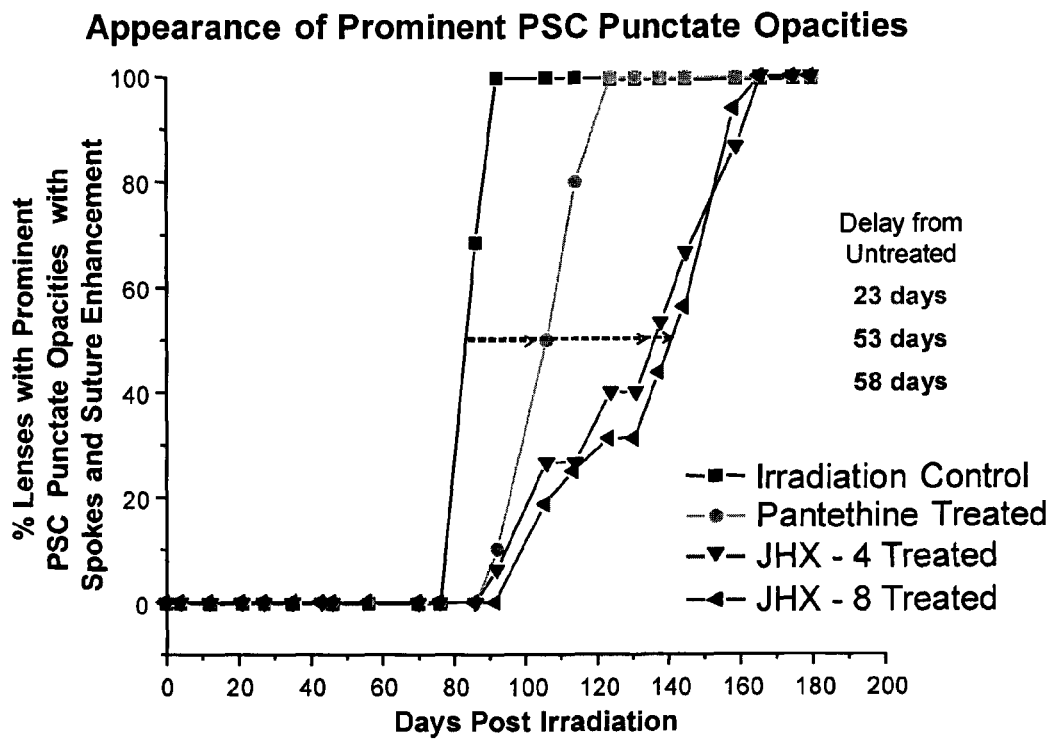
Figure 14B:
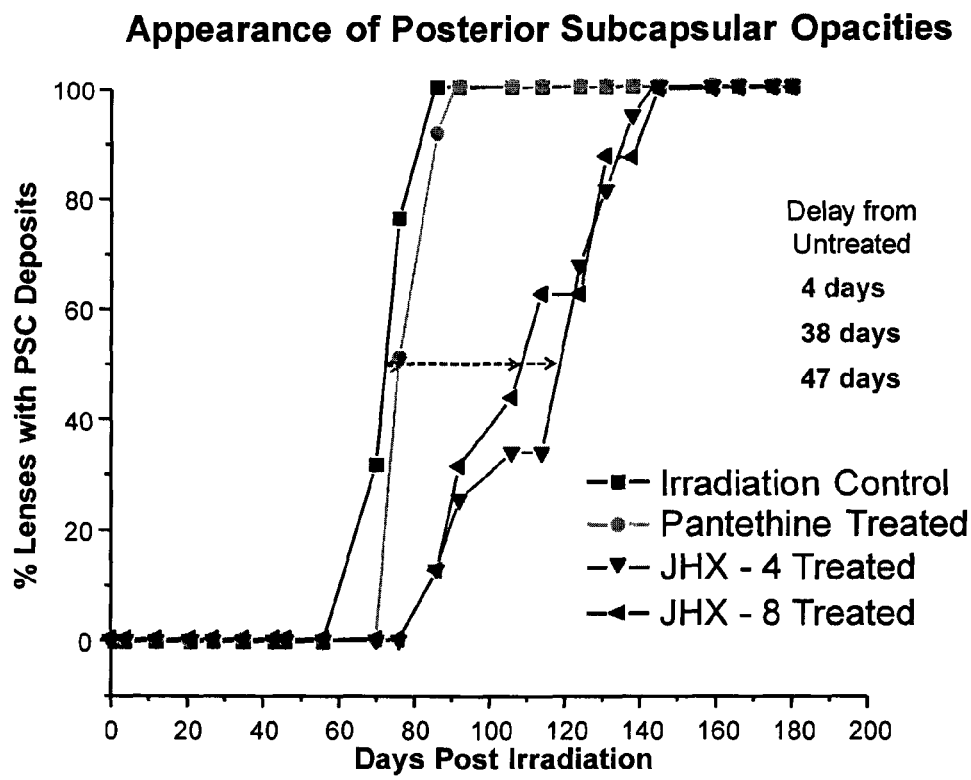

FIGS. 14A and 14B are graphs of the progression of lens changes after irradiation. FIG. 14A shows the appearance of prominent posterior capsular (PSC) punctuate opacities with the presence of spokes and suture enhancement. FIG. 14B shows the appearance of PSC cataracts with the appearance of the blocked retinal vessels.

DETAILED DESCRIPTION OF THE INVENTION

In accordance with the instant invention, a series of analogs of 1-N,N'-dimethylsulfamoyl-4-(2-pyrimidyl)piperazine (JHX-1) were synthesized possessing free radical scavenger (FRS) (JHX-2,-4,-6,-8) or chelating activity (JHX-3,-4,-7,-8) or both (JHX-4,-8) (FIG. 1).

In accordance with one aspect of the instant invention, these compounds can be used for the treatment of cataract and/or macular degeneration (e.g. age-related macular degeneration (AMD)). ROS plays a central role in the development of many cataracts, including age-related, radiation, vitrectomy, and tobacco smoke associated cataracts (Karslioglu et al. (2005) J. Radiat. Res. (Tokyo), 46:277-82; Shalini et al. (1994) Ind. J. Biochem. Biophys., 31:261-6; Truscott, R. J. (2005) Exper. Eye Res., 80:709-25; Ikesugi et al. (2006) Exp. Eye Res., 83:508-16; Boscia et al. (2000) Invest. Opthalmol. Vis. Sci., 41:2461-5). The Fenton reaction is believed to contribute to ROS in many cataracts since Cu and Fe accumulation occurs in the lens (Garner et al. (2000) Exp. Eye Res., 71:599-607; Ciaralli et al. (2001) J. Trace Elem. Med. Biol., 14:205-9) and iron chelation both clinically reduces cataracts in β-thalassemia patients (Popescu et al. (1998) Oftalmologia, 45:10-3), and tobacco smoke exposed rats (Avunduk et al. (1999) Arch. Opthalmol., 117:1368-72). The ring structure of JHX-1 was derived from studies investigating the effect of sorbitol dehydrogenase inhibitor (SDI) on sugar cataract formation (Kador et al; (2004) J. Ocul. Pharmacol. Ther., 20:333-44). By modifying the position the pyridine ring and removing the hydroxymethyl substituent, all SDI activity was abolished. FRS activity was introduced by addition of a —OH group in the 5-position of the pyrimidine ring. This was based on the observation that 5-pyrimidinols are more effective antioxidants than their corresponding phenols with 2-N, N-Dimethyl-4,6-dimethyl-5-hydroxypyrimidine 5-fold more reactive toward alkyl radicals and essentially equally reactive to peroxy radicals compared to α-tocopherol (Gino et al. (2001) J. Am. Chem. Soc., 123:4625-26). Methoxy rather than methyl groups were added to the pyrimidine ring because these cannot be metabolized to a hydroxymethyl group which is required for sorbitol dehydrogenase inhibition. In addition, the methoxy groups stabilize the radical scavenger slightly better than the methyl groups (Bakalbassis et al. (2003) J. Physical. Chem. A, 107:8594-8606; Jinno and Okita (1998) Chem. Pharm. Bull., 46:1688-94; Pedulli and Franco (2001) Trends Org. Chem., 9:97-105). Chelation was introduced by adding carbonyl groups directly adjacent to the amino group connecting the piperazine ring to the pyrimidine ring. This was based on a report that 2-N-succinamide-1,3-pyrimidine easily forms complexes with transition metals such as $Fe^{3+}$ and $Cu^{2+}$ (Zaidi et al. (1993) Inorg. Metal-Organ. Chem., 23:1571-84).

As described in the Examples hereinbelow, the evaluation of JHX-1-JHX-8 in the presence of $Fe^{2+}$, $Fe^{3+}$ $Cu^{1+}$, $Cu^{2+}$, $Zn^{2+}$, $Ca^{2+}$, and $Mg^{2+}$ indicated that only JHX-3, JHX-4, JHX-7, and JHX-8 which possess a 2,8-dioxopiperazine ring bind metal ions. Selective binding was observed with $Cu^{1+}=Cu^{2+}>Fe^{2+}=Fe^{3+}>Zn^{2+}$. There was no binding with either $Ca^{2+}$ or $Mg^{2+}$. In vitro evaluation of all 8 compounds in the human lens epithelium cell line SRA-1 (Ibaraki et al. (1998) Exp. Eye Res., 67:577-85) indicated that compounds containing the FRS groups reduced ROS generated by $H_2O_2$ alone, from the $H_2O_2$—$Fe^{2+}$ Fenton reaction, or homo-cysteine induced endoplasmic reticulum (ER) stress at rates similar to Trolox, a soluble vitamin E analog. ROS protection was demonstrated by reduced $H_2DCF$-DA ROS staining and increased MTA staining of cell viability. These compounds also maintained reduced glutathione (GSH) levels in the lens cells. Compounds possessing chelating groups (JHX-3, JHX-4, JHX-7, and JHX-8) also protected against ROS generated by the $Fe^{2+}$-Fenton reaction. Analogs possessing both FRS and chelating groups reduced Fenton reaction generated ROS slightly better than Trolox.

Six day oral administration of rat chow containing 0.05% of either JHX-4 and JHX-8 to young rats indicated that both compounds enter the lens and the posterior segment (retina and choroid) with levels of JHX-4>JHX-8. However, only trace amounts of either compound entered brain. Subsequent in vivo evaluation of both analogs in diabetic rats demonstrated that both delayed diabetic cataract formation with JHX-4>JHX-8. This delay was proportional to the lens levels of drug achieved. Diabetic cataracts are initiated by the formation of sorbitol by aldose reductase (AR) and AR inhibitors prevent these cataracts (Kador, P. F. (1994) Principles and Practice of Opthalmology, ed. F. A. J. Daniel M. Albert. Vol. Basic Sciences., Philadelphia: W.B. Saunders Co. 146-67; Kador, P. F., ed. Ocular Pathology of Diabetes Mellitus. Duane's Ophtalmology, ed. W. Tasman and E. A. Jaeger. Vol. 3. 2007, Wolters Kluwer/Lippicott Williams and Wilkins: Philadelphia, 1-84). The delay observed with JHX-4 and JHX-8 is due to a reduction in ROS that is generated by ER stress which is induced by sorbitol-linked osmotic stress (Mulhern et al. (2006) Invest. Opthalmol. Vis. Sci., 47:3951-9). JHX-4 and JHL-8 treatment did not alter blood sugar or lens sorbitol levels.

While preliminary studies suggest that these multifunctional antioxidants may also be beneficial for the treatment of ROS linked neurodegeneration, in vivo accumulation into the brains of normal rats is minimal. The blood brain barrier (BBB) is highly restrictive with >98% of all small drugs and almost all large molecules medicinally developed failing to cross. A standard method for improving BBB penetration is lipidization, i.e., making molecules more lipophilic or using lipid carriers attached to water-soluble drugs (Witt et al. (2001) Peptides, 22:2329-43; Bodor et al. (1992) Science, 257:1698-700). In general, the drug BBB permeability decreases 1 log order for each pair of H-bonds added in the form of polar functional groups to a molecule (Pardridge and Mietus (1979) J. Clin. Invest., 64:145-54). Based on H-bonding rules (Stein, W. D., The movement of molecules across cell membranes. 1967, New York: Academic Press 369; Diamond and Wright (1969) Proc. Royal Soc. London Ser. B, 171:273-316), the number of H-bonds that a given drug forms with water can be calculated from the chemical structure. Compounds with H-bonds >8 are unlikely to cross the BBB in pharmacologically significant amounts via lipid-mediated free diffusion (Pardridge, W. M., (2007) Drug Discov. Today, 12:54-61). Another well-established parameter is the molecule weight (MW) (Fischer et al. (1998) J. Membr. Biol., 165:201-11; Hingson and Diamond (1972) J. Membr. Biol., 10:93-135; Cohen and Bangham (1972) Nature, 236:173-4). When the drug MW is >400, its BBB permeability does not increase in proportion to lipid solubility.

Another widely used descriptor of lipophilicity is the octanol-water partition coefficient, P, which is a measure of the differential solubility of a neutral substance between these immiscible liquids. It is generally used in its logarithmic form, logP, with LogP=1 indicating a 10:1 Organic:Aqueous solubility, a LogP=0 indicating an equal, 1:1 Organic:Aqueous solubility and LogP=−1 indicating a 1:10 Organic:Aqueous solubility (Hansch, C. (1971) Med. Chem., Ser. Monogr., 11:271-342; Leo et al. (1971) Chem. Rev., 71:525-616). Drug candidates are often screened according to logP because lipophilicity is a major determining factor in a compound's absorption, distribution in the body, penetration across vital membranes and biological barriers, metabolism and excretion (ADME properties) (Desai et al. (1991) Bioorg. Med. Chem. Lett., 1:411-14; Lipinski et al. (1997) Adv. Drug Delivery Rev., 23:3-25). For drugs targeting the CNS, the ideal logP is a value around 2 (Hansch et al. (1987) J. Pharm. Sci., 76:663-87) while for oral and intestinal absorption the idea value is 1.35-1.8.

Calculated estimations of logP, conducted with Cambridgesoft ChemBioDraw Ultra ver. 11 software, were performed for the compounds depicted in FIG. 2. In the unsubstituted pyrimidine ring series (left column, FIG. 2), the logP values decrease on from p-chlorophenyl, 0.85>phenyl, 0.29>benzyl, 0.20>cyclohexyl, 0.01>butyl, −0.29>allyl, −0.84>1,4-dihydrotrigonellate −1.48>methyl, −1.53>N,N-dimethylsulfamoyl (JHX-4), −2.75. For the dimethoxy series (second column of FIG. 2), the logP values decrease on from p-chlorophenyl, 2.30>phenyl, 1.47>benzyl, 1.37>cyclohexyl, 1.19>butyl, 0.89>allyl, 0.34>methyl, −0.38>1,4-dihydrotrigonellate, −0.30>N,N-dimethylsulfamoyl (JHX-8), −2.39. These calculations indicate that substitution of the N,N-dimethylsulfamoyl group greatly increases lipophilicity, particularly with the dimethoxy series. Notably, the p-chlorophenyl, phenyl, benzyl, and cyclohexyl analogs in the dimethoxy series fall within the ideal ranges for optimal entry into the CNS. Both JHX-4 and JHX-8 are highly water soluble with dimethoxy substitution making little difference. Nevertheless, both are biologically active in the lens and retina.

Dihydrotrigonellinate analogs are unique not only because they alter the lipophilicity of JHX-4 and JHX-8, but because they can serve as a chemical delivery system (CDS) that can "trap" the compounds in the brain. This carrier molecule is specially designed, to undergo an enzymatically mediated oxidation that converts the membrane-permeable dihydrotrigonellinate to a hydrophilic, membrane-impermeable trigonellinate salt. This conversion occurs ubiquitously and the now polar oxidized group becomes trapped behind the lipoidal BBB i.e., the trigonellinate salt group connected to the multifunctional antioxidant is depoted in the CNS (Brewster and Bodor (1992) NIDA Res. Monogr., 120:169-201). In contrast, those compounds containing the oxidized salt in the periphery will be rapidly lost as it is now polar and an excellent candidate for elimination by the kidney and liver.

An alternate approach to drug lipidization is the facilitated transport of drugs into the CNS at the BBB through specific carrier systems (de Boer and Gaillard (2007) Annu. Rev. Pharmacol. Toxicol., 47:323-55). This approach has been used to introduce anti-neoplastic drugs into the brain by coupling the alkylating agent melphalan with phenylalanine (Greig et al., (1987) Cancer Res., 47:1571-6). As such, the N,N-dimethylsulfamoyl-group of JHX-4 and JHX-8 may be substituted with a phenylalanine moiety which utilizes the system L transporter (e.g.,

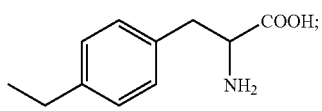

large, neutral amino acids; Kanai and Endou (2003) J. Tox. Sci., 28:1-17), with an adenine moiety (e.g.,

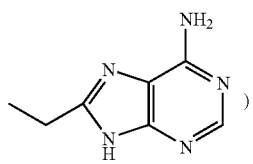

which utilizes the purine transport system, with a lactic acid moiety (e.g.,

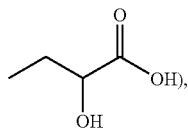

or a salicylic acid moiety (e.g.,

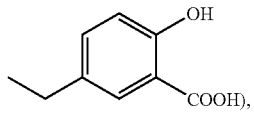

both of which utilize the monocarboxylate transport (MCT) system at the BBB.

The MW of the compounds presented in FIG. 2 are under 400. Moreover, the replacement of 1-N,N'-dimethylsulfamoyl-substituent reduces the H-bond number to 4 for the unsubstituted pyrimidine ring series and to 6-H bonds for the dimethoxy series, except for those compounds with a 1,4-dihydrotrigonellate, wherein the H-bond number is 5 and 7, respectively. Based on these parameters, all compounds should cross the BBB via lipid-mediated diffusion.

DEFINITIONS

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, preservative, solubilizer, emulsifier, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions may be employed as carriers. Suitable pharmaceutical carriers are described in "Remington's Pharmaceutical Sciences" by E. W. Martin.

The term "alkyl," as employed herein, includes linear, branched, and cyclic (see cycloalkyl below) chain hydrocarbons containing about 1 to 10 carbons, preferably 1 to 8 carbons, more preferably 1 to 4 carbons (a "lower alkyl"), in the normal chain. An alkyl may be referred to as a hydrocarbyl. Examples of suitable alkyl groups include methyl, ethyl, propyl, isopropyl, butyl, t butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may optionally be substituted with 1 to 4 substituents which include, for example, halo (such as F, Cl, Br, I), haloalkyl (such as $CCl_3$ or $CF_3$), alkyl, alkoxy, hydroxy, aryl, aryloxy, aralkyl, cycloalkyl, alkylamido, alkanoylamino, oxo, acyl, arylcarbonylamino, amino (—$NH_2$), substituted amino, nitro, cyano, carboxy (—COOH), carbonyl (—C(=O)), epoxy, urea (—NH-$CONH_2$), thiol (—SH), alkylthio, alkyloxycarbonyl (—C (=O)—OR), alkylcarbonyloxy (—OC(=O)—R), carbamoyl ($NH_2C$(=O)— or NHRC(=O)—), and/or alkylurea (—NHCONHR), wherein R in the aforementioned substituents represents an alkyl radical. The alkyl group may optionally comprise one or more carbon to carbon double bonds (i.e., the alkyl group may be unsaturated). The alkyl may also comprise at least one (e.g., from 1 to about 4) sulfur, oxygen, or nitrogen heteroatoms within the hydrocarbon chain. For example, the alkyl can be —OR, —SR, or —NHR, wherein R is a hydrocarbon chain.

The term "cycloalkyl," as employed herein, includes saturated or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), preferably 3 to 10 carbons forming the ring(s), and may optionally be fused to 1 or 2 aromatic rings as described for aryl, below. Unsaturated cycloalkyl groups may contain one or more double bonds and/or triple bonds. Cycloalkyl groups include, without limitation, cyclopropyl, cyclobutyl, cyclopentyl, cyclohexyl, cycloheptyl, cyclooctyl, cyclodecyl and cyclododecyl, cyclopentenyl, cyclohexenyl, cycloheptenyl, cyclooctenyl, cyclohexadienyl, and cycloheptadienyl. Each cycloalkyl group may be optionally substituted with substituents such as halogen, alkyl, alkoxy, hydroxy, aryl, aryloxy, aralkyl, cycloalkyl, alkylamido, alkanoylamino, oxo, acyl, arylcarbonylamino, amino, substituted amino, nitro, cyano, thiol and/or alkylthio. The cycloalkyl may also comprise at least one (e.g., from 1 to about 4) sulfur, oxygen, or nitrogen heteroatoms within the hydrocarbon chain.

The term "aryl," as employed herein, refers to monocyclic and bicyclic aromatic groups containing 6 to 10 carbons in the ring portion. Examples of aryl groups include, without limitation, phenyl or naphthyl, such as 1 naphthyl and 2 naphthyl, or indenyl. Aryl groups may optionally include one to three additional rings fused to a cycloalkyl ring or a heterocyclic ring. Aryl groups may be optionally substituted through available carbon atoms with 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocylooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

The terms "halogen," "halo," and "halide" refer to chlorine, bromine, fluorine or iodine.

The term "treating" refers to delaying, halting, and/or reversing the progression of a disease and/or condition.

The term "preventing" refers to the slowing of the development of disease symptoms, delaying the onset of the disease or condition, halting the progression of disease development, and/or preventing the host from developing the disease or condition at all.

Compounds

In accordance with one embodiment of the instant invention, compounds are provided of the formula:

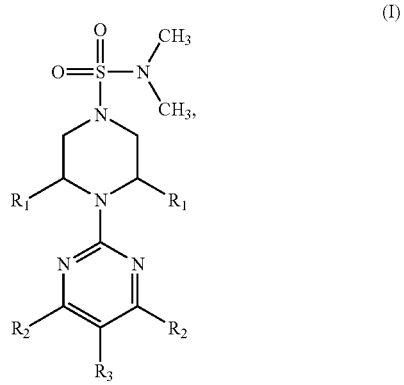

(I)

wherein $R_1$ is =O or comprises two moieties independently selected from the group consisting of H, halo, thiol, carboxy, nitro, amino, cyano, hydroxyl, alkyl, and aryl, wherein $R_2$ is selected from the group consisting of H, halo, thiol, carboxy, nitro, amino, cyano, hydroxyl, alkyl, and aryl, and wherein $R_3$ is selected from the group consisting of H, halo, thiol, carboxy, nitro, amino, cyano, hydroxyl, alkyl, and aryl. In a particular embodiment, when $R_3$ is H, and $R_2$ is H or $OCH_3$, then $R_1$ is not H,H. In another embodiment, $R_1$ is H,H or =O, preferably =O. In another embodiment, $R_2$ is H, halo, thiol, carboxy, nitro, amino, cyano, hydroxyl, or a lower alkyl. $R_2$ may also be H, —OR, —SR, or —NHR, wherein R is H or a lower alkyl. In still another embodiment, $R_2$ is H or $OCH_3$. In another embodiment, $R_3$ is H, —OR, —SR, or —NHR, wherein R is H or a lower alkyl, preferably H or OH, and more preferably OH. In yet another embodiment, $R_1$ is H,H or =O; $R_2$ is H or $OCH_3$; and $R_3$ is H or OH. In a particular embodiment, $R_1$ is =O; $R_2$ is H, —OR, —SR, or —NHR, wherein R is H or a lower alkyl, particularly where $R_2$ is H or $OCH_3$; and $R_3$ is OH. While formula I depicts that both $R_1$ groups are the same and that both $R_2$ groups are the same, the two $R_1$ groups can be considered $R_{1A}$ and $R_{1B}$ and the two $R_2$ groups can be considered $R_{2A}$ and $R_{2B}$ and be independently selected from the listed substituents.

In accordance with another embodiment of the instant invention, compounds are provided of the formula:

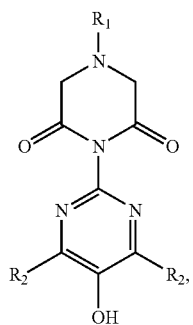

(II)

wherein $R_1$ is selected from the group consisting of H, halo, thiol, carboxy, nitro, amino, cyano, hydroxyl, alkyl, and aryl and $R_2$ is selected from the group consisting of H, halo, thiol, carboxy, nitro, amino, cyano, hydroxyl, alkyl, and aryl. In a particular embodiment, $R_1$ is an alkyl, particularly a cycloalkyl, or aryl. In another embodiment, $R_2$ is H, halo, thiol, carboxy, nitro, amino, cyano, hydroxyl, or a lower alkyl. $R_2$ may also be H, —OR, —SR, or —NHR, wherein R is H or a lower alkyl. In still another embodiment, $R_2$ is H or $OCH_3$. In yet another embodiment, $R_1$ is an alkyl, cycloalkyl, or aryl and $R_2$ is H or $OCH_3$. While formula II depicts that both $R_2$ groups are the same, the two $R_2$ groups can be considered $R_{2A}$ and $R_{2B}$ and be independently selected from the listed substituents. Further, in another particular embodiment, the =O and —OH groups of formula II are varied as in formula I.

In a particular embodiment, $R_1$ of formula II is selected from the group consisting of a lower alkyl, cyclohexyl, a phenyl optionally linked via a lower alkyl, a halo substituted phenyl, an adenine moiety optionally linked via a lower alkyl, a salicylic acid moiety optionally linked via a lower alkyl, and a large neutral amino acid (e.g., phenylalanine, tryptophan, leucine, methionine, isoleucine, tyrosine, histidine, valine, threonine, proline, asparagine, glutamine, and/or analogs or derivatives thereof) optionally linked via a lower alkyl. In yet another embodiment, $R_1$ is selected from the group consisting of methyl, butyl, allyl, cyclohexyl, phenyl, chlorophenyl, benzyl,

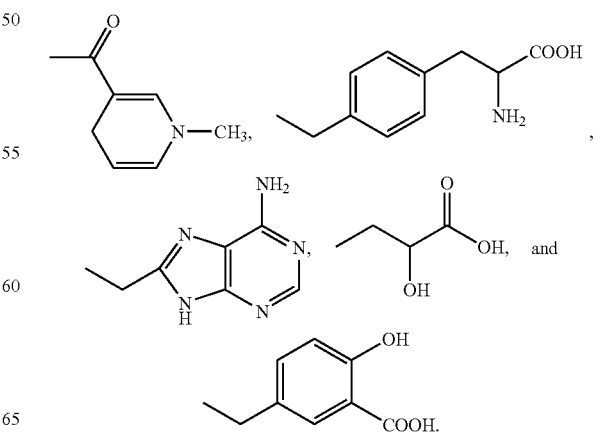

In accordance with another embodiment of the instant invention, compounds are provided of the formula:

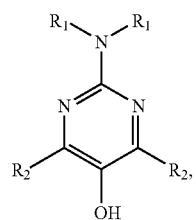

(III)

wherein $R_1$ is selected from the group consisting of H, halo, thiol, carboxy, nitro, amino, cyano, hydroxyl, alkyl, and aryl, and wherein $R_2$ is selected from the group consisting of H, halo, thiol, carboxy, nitro, amino, cyano, hydroxyl, alkyl, and aryl. In a particular embodiment, $R_2$ is H, halo, thiol, carboxy, nitro, amino, cyano, hydroxyl, or a lower alkyl. $R_2$ may also be H, —OR, —SR, or —NHR, wherein R is H or a lower alkyl. In still another embodiment, $R_2$ is H or $OCH_3$. While formula III depicts that both $R_1$ groups are the same and that both $R_2$ groups are the same, the two $R_1$ groups can be considered $R_{1A}$ and $R_{1B}$ and the two $R_2$ groups can be considered $R_{2A}$ and $R_{2B}$ and be independently selected from the listed substituents. Further, the $R_1$ groups can form a ring structure such as an aryl or cycloalkyl. In a preferred embodiment, the compound of formula III is an antioxidant (see, e.g., U.S. Pat. No. 7,084,100).

Compositions of the instant invention comprise at least one compound of formula I, II, and/or III and at least one pharmaceutically acceptable carrier.

Methods of synthesizing compounds of formula I are provided hereinbelow in Example I. Exemplary methods for synthesizing compounds of formula II are outlined generally hereinbelow.

N-alkyliminodiacetic acids may be converted to anhydrides in the presence of acetic anhydride using the methods described hereinbelow in the synthesis of JHX-3. The anhydrides can be reacted with a 2-aminopyrimidine to give the respective 2,6-dioxopiperazine according to published methods (Henry, D. W. (1966) J. Heterocycl. Chem., 3:503-11) that were similarly used in the synthesis of JHX-4, described hereinbelow. The 5-acetoxy protecting group on the pyrimidine ring may be removed by hydrolysis with potassium carbonate to give the desired products (Buechi et al. (1971) J. Amer. Chem. Soc., 93:3299-301).

As stated hereinabove, 1,4-dihydrotrigonellinates have proved to be a very useful moiety as a lipophilicity modifier to deliver many small molecular drugs that can not cross BBB to brain (Brewster et al. (1993) Chemical Approaches to Brain-Targeting of Biologically Active Compounds. Drug design for neuroscience, ed. A. P. Kozikowski, New York Raven Press. 480; Brewster et al. (1988) J. Med. Chem., 31:244-9; Palomino et al. (1989) J. Med. Chem., 32:622-5; Chen et al. (1998) J. Med. Chem., 41:3773-81; Pop et al. (1989) J. Med. Chem., 32:1774-81). In vivo, 1,4-dihydrotrigonellinates are oxidized to a membrane-impermeable trigonellinate salt. When this oxidation occurs in the brain, drugs containing the trigonellinate group become depoted in the brain (Brewster and Bodor (1992) NIDA Res. Monogr., 120:169-201). The synthesis of the 4-(1,4-dihydrotrigonellate)-2,6-dioxo-piperazine may be conducted as follows. Nicotinic acid (niacin) can be esterified (Lee et al. (2002) Synth. Commun., 32:2209-2213) and the nitrogen may be methylated and reduced (Brewster et al. (1989) J. Org. Chem., 54:3721-6) to give methyl 1-methyl-1,4-dihydropyridine-3-carboxylate. The ester may then be hydrolyzed to the acid (Pfaendler and Jenni (1999) Heterocycles, 50:867-874). Treatment of the acid with thionyl chloride as reported by Kruse will form the acid chloride which can be readily reacted with (5-hydroxy-2-pyrimidyl)piperazine-2,6-diones to give the desired products 4-(1,4-dihydrotrigonel-late)-2,6-dioxopiperazines (Kruse et al. (1988) Recl. Trav. Chim. Pays-Bas, 107:303-9; Komoto et al. (2000) Chem Pharm Bull (Tokyo), 48:1978-85). (5-Hydroxy-2-pyrimidyl)piperazine-2,6-diones may be obtained by hydrogenolysis of 4-benzylpiperazine-2,6-diones.

As stated hereinabove, the 1-N,N'-dimethylsulfamonyl-group of JHX-4 and JHX-8 may also be replaced with endogenous agents (e.g., LNAAs such as phenylalanine, adenine, lactic acid, and salicylic acid) that utilize facilitated transport systems at the BBB. The carrier mediated transport systems present in the BBB are primarily responsible for the transport of endogenous substances and nutrients across the BBB into the brain. These systems can be exploited for delivering drugs into the brain (Pardridge, W. M., (2007) Drug Discov. Today, 12:54-61; de Boer and Gaillard (2007) Annu. Rev. Pharmacol. Toxicol., 47:323-55; Ohtsuki and Terasaki (2007) Pharm. Res., 24:1745-58; Greig et al. (1987) Cancer Res., 47:1571-6; Tsuji, A. (2005) NeuroRx, 2:54-62). Use of facilitated transport of drugs into the CNS at the BBB through specific carrier systems is an alternative to lipidization. At the BBB, phenylalanine utilizes the System L transporter adenine utilizes the purine transport system, lactic acid and salicylic acid utilize the monocarboxylate transport (MCT) system (Betz, A. L. (1992) NIDA Res. Monogr., 120:54-72). Compounds may be synthesized by nucleophilic substitution of (5-hydroxy-2-pyrimidyl)-piperazine-2,6-diones with either Cl- or Br-substituted analogs transport substrates according to Ho et al. (Ho et al. (2004) Bioorg. Med. Chem. Lett., 14:545-8). 4-(Bromomethyl)phenylalanine may be obtained from commercially available 4-(hydroxymethyl)-phenyl-alanine according to Gribble et al. (Gribble et al. (1985) J. Org. Chem., 50:1611-16).

Treatment

The instant invention encompasses methods of treating and/or preventing cataract, macular degeneration, neurodegeneration, and/or injury associated with radiation exposure. The methods comprise administering a composition comprising at least one compound comprising 5-hydroxyl-2-amino-1,3-pyrimidine (i.e., a pyrimidinol). For example, the administered compound is of formula I, II, and/or III. The methods may optionally further comprise monitoring said patient to determine the efficacy of cataract treatment, macular degeneration treatment, neurodegeneration treatment, or radiation exposure treatment.

In one embodiment, compounds of the instant invention (e.g., compounds of formulas I, II, or III) can be used to treat and/or prevent cataract and/or macular degeneration by administering said compound to a patient in need thereof. In a particular embodiment, the method comprises administering a composition comprising at least one compound of formula I, II, and/or III and at least one pharmaceutically acceptable carrier. In another embodiment, the composition comprises at least one compound of formula I, particularly wherein $R_1$ is H,H or =O; $R_2$ is H or $OCH_3$; and $R_3$ is H or OH, with the proviso that if $R_3$ is H, then $R_1$ cannot be H,H. In a preferred embodiment, the composition comprises at least one compound of formula I wherein $R_1$ is =O and $R_3$ is OH. Such a pharmaceutical composition may be administered, in a therapeutically effective amount, to a patient in need thereof for the treatment and/or prevention of cataract. Other anticataract agents (e.g., pirenoxine and the like) may be administered concurrently (e.g., in the same composition) or sequentially with the compounds of the instant invention. Additionally, other antioxidants may be administered concurrently (e.g., in the same composition) or sequentially with the compounds of the instant invention.

In another embodiment, compounds of the instant invention (e.g., compounds of formula I, II, and/or III) can be used to treat and/or prevent neurodegenerative disorders by administering the composition to a patient. In a particular embodiment, the method comprises administering a composition comprising at least one compound of formula I, II, and/or III and at least one pharmaceutically acceptable carrier. In a particular embodiment, the compound is of formula II. Other agents for the treatment of neurodegenerative disorders may be administered concurrently (e.g., in the same composition) or sequentially with the compounds of the instant invention.

Neurodegenerative disorders that can be treated and/or prevented by the instant methods include, without limitation, Alzheimer's disease, Parkinson's disease, Lewy Body disease, prion disease, amyotrophic lateral sclerosis, cerebral amyloid angiopathy, inclusion body myositis, macular degeneration, mild cognitive impairment (MC1), Down's syndrome, seizure, neuropathic pain, Abercrombie's degeneration, acquired epileptiform aphasia, Landau-Kleffner syndrome, acute disseminated encephalomyelitis, adrenoleukodystrophy, leukodystrophy, agnosia, Alexander disease, Alpers' Disease, progressive sclerosing poliodystrophy, alternating hemiplegia, Lou Gehrig's disease, Angelman syndrome, ataxia telangiectasia, ataxias and cerebellar/spinocerebellar degeneration, attention deficit disorder, Binswanger's disease, subcortical dementia, canavan disease, cerebral hypoxia, cerebro-oculo-facio-skeletal syndrome, Pena Shokeir II syndrome, Charcot-Marie-Tooth, chronic inflammatory demyelinating polyneuropathy (CIDP), corticobasal degeneration, Creutzfeldt-Jakob disease, degenerative knee arthritis, diabetic neuropathy, early infantile epileptic encephalopathy, Ohtahara syndrome, epilepsy, Friedreich's ataxia, Guillain-Barre syndrome (GBS), acute idiopathic polyneuritis, Hallervorden-Spatz disease, neurodegeneration with brain iron accumulation, Huntington's disease, Krabbe disease, Kugelberg-Welander disease, spinal muscular atrophy (SMA), SMA type I, SMA type II, SMA type III, Kennedy syndrome, progressive spinobulbar muscular atrophy, Congenital SMA with arthrogryposis, adult SMA, Leigh's disease, Lennox-Gastaut syndrome, Machado-Joseph disease, spinocerebellar ataxia type 3, Monomelic Amyotrophy, multiple sclerosis, neuroacanthocytosis, Niemann-Pick disease, olivopontocerebellar atrophy, paraneoplastic Syndromes, neurologic paraneoplastic syndromes, Lambert-Eaton myasthenic syndrome, stiff-person syndrome, encephalomyelitis, myasthenia gravis, cerebellar degeneration, limbic and/or brainstem encephalitis, neuromyotonia, opsoclonus and sensory neuropathy, Pelizaeus-Merzbacher disease, Pick's disease, primary lateral sclerosis, progressive locomotor ataxia, syphilitic spinal sclerosis, Tabes Dorsalis, progressive supranuclear palsy, Rasmussen's encephalitis, Rett syndrome, Tourette's syndrome, Usher syndrome, West syndrome, infantile spasms, Wilson disease, and hepatolenticular degeneration. In a particular embodiment, the neurodegenerative disorder is selected from the group consisting of Alzheimer's disease, Parkinson's disease, Lewy Body disease, amyotrophic lateral sclerosis, and prion disease.

In yet another embodiment, compounds of the instant invention (e.g., compounds of formula I, II, and/or III) can be used to treat and/or prevent disorders, symptoms, and/or injury associated with exposure to radiation by administering the composition to a patient (i.e., the compounds of the instant invention are radioprotective agents). In a particular embodiment, the method comprises administering a composition comprising at least one compound of formula I, II, and/or III and at least one pharmaceutically acceptable carrier. In yet another embodiment, the composition comprises at least one compound of formula I, particularly when $R_1$ is $=$O and $R_3$ is OH. Other radioprotective agents (e.g., amifostine) may be administered concurrently (e.g., in the same composition) or sequentially with the compounds of the instant invention.

As used herein, "radiation" refers to ionizing radiation caused by high-energy electromagnetic waves (e.g., X-rays, gamma rays) or particles (e.g., alpha particles, beta particles, neutrons). Radiation can be emitted by radioactive substances (radioisotopes; e.g., uranium, radon, and plutonium) and can be produced by man-made sources, such as x-ray and radiation therapy machines (e.g., radiotherapy for cancer treatment). Radioprotective agents may be defined as compounds that are administered before exposure to ionizing radiation to reduce its damaging effects. In a particular embodiment, the compounds of the instant invention are administered to a patient prior to exposure of ionizing radiation to treat, prevent and/or lessen symptoms/injuries associated with radiation exposure such as acute radiation illness. For example, symptoms associated with acute radiation illness include, without limitation, loss of appetite, weight loss, lethargy, nausea, vomiting, fatigue, weakness, and dry mouth. In another embodiment of the instant invention, the compounds of the instant invention prevent and/or lessen the damage to the salivary glands due to radiation exposure.

The compositions of the instant invention can be administered prior to a known exposure of radiation (e.g., a patient undergoing radiotherapy (e.g., for the treatment of cancer) or as a preventative measure to an undetermined exposure (e.g., as a precaution to a terrorist attack or as a precautionary measure for the military).

The pharmaceutical compositions of the present invention can be administered by any suitable route, for example, by injection (e.g., intravenously and intramuscularly), by oral, pulmonary, nasal, rectal, or other modes of administration. In a preferred embodiment, for the treatment of cataract and/or macular degeneration, the compositions of the instant invention are administered orally or directly to the eye (e.g., in eye drops). When administered orally, compositions of the instant invention may be, for example, in pill form (e.g., capsule, tablet, and lozenge, optionally time-released), a solid, a powder, a solution, a syrup, an emulsion, a dispersion, a micelle, a liposome, or any other form suitable for use. Common carriers include, without limitation, water, oil, buffered saline, ethanol, polyol (for example, glycerol, propylene glycol, liquid polyethylene glycol and the like), dimethyl sulfoxide (DMSO), detergents, suspending agents, glucose, lactose, gum acacia, gelatin, mannitol, starch paste, magnesium trisilicate, talc, corn starch, keratin, colloidal silica, potato starch, urea, medium chain length triglycerides, dextrans, other carriers suitable for use in manufacturing preparations, in solid, semisolid, or liquid form, and suitable mixtures thereof. In addition excipients and auxiliary, stabilizing, preserving, thickening, flavoring, and coloring agents may be included in the compositions.

The following examples describe illustrative methods of practicing the instant invention and are not intended to limit the scope of the invention in any way.

EXAMPLE I

Synthesis Protocols

NMR spectra were obtained with a Varian 500 MHz spectrometer. Electro impact-mass spectrometry (EI-MS) utilized an Agilent 5973N MSD, and electrospray ionization-mass spectrometry (ESI-MS) was conducted with a Finnigan MAT LCQ. Melting points were uncorrected. Column chromatography (CC) utilized Merck silica gel (230-400 mesh). Elemental analyses done by M-H—W Laboratories, *Phoenix, Ariz.*

Synthesis of 1-N,N'-dimethylsulfamoyl-4-(2-pyrimidyl)piperazine (JHX-1)

This compound was synthesized as previously described (Kador et al. (2004) J. Ocul. Pharmacol. Ther., 20:333-44). Briefly, piperazine was converted to piperazine-1-sulfonic acid dimethylamide which was then reacted with 2-chloropyrimide to give JHX-1 in 75% yield. The structure was confirmed by $^1$H-NMR, $^{13}$C-NMR, ESI-MS and elemental analysis.

Synthesis of 1-N,N'-dimethylsulfamoyl-4-(5-hydroxy-2-pyrimidyl)piperazine (JHX-2)

Step 1: Triethylamine (7.2 mL, 51.8 mmol) was added to a solution of piperazine-1-sulfonic acid dimethyl amide (10 g, 51.8 mmol) dissolved in 400 mL of THF. 2-chloro-5-nitropyrimidine (7.7 g, 48.3 mmol) dissolved in 20 mL of THF was added to the stirred mixture. After 24 hours stirring at room temperature (RT), THF was removed under vacuum and 600 mL of $CHCl_3$ was added to the residue. The $CHCl_3$ layer was washed with 0.5 N HCl and brine, dried over $Na_2SO_4$, and filtered. Solvent evaporation gave 14.1 g (92%) of straw yellow solid 1-N,N'-dimethylsulfamoyl-4-(2-(5-nitropyrimidyl)piperazine. The structure was confirmed by $^1$H-NMR. $^1$H NMR ($CDCl_3$) δ9.08 (s, 2H), 4.09 (appt, J=5.13 Hz, 4H), 3.35 (appt, J=5.13 Hz, 4H), 2.87 (s, 6H). Step 2: $NH_4Cl$ (1.43 g, 26.76 mmol) was added to a suspension of 1-N,N'-dimethylsulfamoyl-4-(2-(5-nitropyrimidyl)piperazine (14.1 g, 44.6 mmol) in a mixture of EtOH (175 mL) and $H_2O$ (48 mL), followed by iron powder (7.5 g, 133.9 mmol). After refluxing 1 hour, the reaction mixture was filtered and concentrated to give a brown solid which was dissolved in 800 mL of $CHCl_3$, washed with $NaHCO_3$ and brine, dried over $Na_2SO_4$, and filtered. Solvent evaporation gave a yellow solid which after CC with 100:1 $CHCl_3$:MeOH gave 11.5 g (90%) of solid yellow 1-N,N'-dimethylsulfamoyl-4-(2-(5-nitro-pyrimidyl)-piperazine. The structure was confirmed by $^1$H-NMR and EI-MS. $^1$H NMR ($CDCl_3$) δ7.98 (s, 2H), 3.76 (t, J=4.88 Hz, 4H), 3.30 (t, J=4.88 Hz, 4H), 2.86 (s, 6H); EI-MS (m/z) 286 ($M^+$). Step 3: A suspension of 1-N,N'-dimethylsulfamoyl-4-(2-(5-nitro-pyrimidyl)-piperazine (5.76 g, 20.2 mmol) in 100 mL of 2 M $H_2SO_4$ was refluxed for 1.5 hours until the suspension became clear. After cooling to RT, the solution pH was adjusted to 6-7 with 10 N NaOH, and the cloudy mixture was extracted with EtOAc. The combined organic layers were washed with brine, dried over $Na_2SO_4$, and filtered. Solvent evaporation gave a yellow solid, which was purified by CC using 1:1 EtOAc:hexane to yield 3.23 g (56%) of white solid JHX-2, mp 134-135° C. The structure was confirmed by $^1$H-NMR, $^{13}$C-NMR, ESI-MS and elemental analysis. $^1$H NMR ($CDCl_3$) δ8.08 (s, 2H), 3.78 (appt, J=5.13 Hz, 4H), 3.29 (appt, J=5.13 Hz, 4H), 2.86 (s, 6H); $^{13}$C NMR ($CDCl_3$) 156.9, 145.8, 143.5, 46.0, 44.3, 38.1; EI-MS (m/z) 287 ($M^+$).

Synthesis of 1-N,N'-dimethylsulfamoyl-4-(2-pyrimidyl)piperazine-2,6-dione (JHX-3)

Step 1: A suspension of N-benzyliminodiacetic acid (1.1 g, 5 mmol) in 5.2 mL of $Ac_2O$ was refluxed for 20 minutes until the solution became clear. After removal of $Ac_2O$ under vacuum at 60° C., the remaining yellow oil was dissolved in 5 mL of toluene. A solution of 2-aminopyrimidine (475 mg, 5 mmol) dissolved in 5 mL of acetone was then added and the mixture was refluxed for 5 hours. Solvent evaporation gave a red oil, which was purified by CC using 40:1 $CHCl_3$:MeOH as eluent to yield 1.33 g (88%) of yellow solid iminodiacetic acid monoamide. $^1$H NMR (DMSO-$d_6$) δ10.47 (s, 1H), 8.66 (s, 2H), 8.32 (s, 1H), 7.35-7.19 (m, 5H), 3.84 (s, 2H), 3.50 (s, 2H), 3.39 (s, 2H). Step 2: A suspension of iminodiacetic acid monoamide (1.33 g, 4.4 mmol) in 7 mL of $Ac_2O$ was then refluxed for 4 hours until clear. After cooling to room temperature, $Ac_2O$ was removed under vacuum at 60° C. and the residue was purified by CC using $CHCl_3$ as eluent to yield 743 mg (59%) of white solid. $^1$H NMR ($CDCl_3$) δ8.89 (d, J=4.88 Hz, 2H), 7.42 (t, J=4.88 Hz, 1H), 7.38-7.31 (m, 5H), 3.76 (s, 2H), 3.60 (s, 4H); EI-MS (m/z) ($M^+$–1). Step 3: 10% Pd/C catalyst (248 mg) was added to the white solid (743 mg, 2.6 mmol) dissolved in a MeOH (30 mL) EtOAc (10 mL) mixture and hydrogenated for 12 hours hydrogenated at room temperature. After, filtration of the reaction mixture and solvent evaporation, the remaining solid was purified by CC with 40:1 $CHCl_3$:MeOH as eluent to give 404 mg (81%) of white solid 2-pyrimidyl)piperazine-2,6-dione. $^1$H NMR (DMSO-$d_6$) δ8.96 (d, J=4.88 Hz, 2H), 7.64 (t, J=4.88 Hz, 1H), 3.71 (s, 2H), 3.70 (s, 2H), 3.46 (s, 1H) EI-MS (m/z) 192 ($M^+$). Step 4: $KHCO_3$ (900 mg, 9 mmol) was added to a solution of 2-pyrimidyl)piperazine-2,6-dione (858 mg, 4.46 mmol) dissolved in 25 mL of MeCN, followed by dimethyl-sulfamoyl chloride (9 mL, 9 mmol). The reaction mixture was heated to 60° C. for 24 hours. After cooling to room temperature, filtration, solvent evaporation, and recrystallization form EtOAc 845 mg (63%) white solid JHX-3 was obtained, mp 179-181° C. $^1$H NMR ($CDCl_3$) δ8.90 (d, J=4.88 Hz, 2H), 7.45 (t, J=4.88 Hz, 1H), 4.31 (s, 4H), 2.96 (s, 6H); $^{13}$C NMR ($CDCl_3$) 167.0, 159.5, 154.8, 121.4, 49.5, 38.3; ESI-MS (m/z) 322 ([M+Na]$^+$).

Synthesis of 1-N,N'-dimethylsulfamoyl-4-(5-hydroxy-2-pyrimidyl)piperazine-2,6-dione (JHX-4)

Step 1: $PCl_5$ (42.0 g, 200 mmol) was added in portions to 1,1,2-trimethoxyethane (25.2 mL, 200 mmol) maintained below 30° C. The mixture was then heated to 60° C. for 75 minutes followed by cooling to 0° C. 45 mL of DMF (600 mmol) was drop-wise added and the mixture was stirred at room temperature for 30 minutes, followed by stirring for 45 minutes at 70° C. After cooling, 200 mL of MeOH was added at 0° C., followed by NaOH (60 g, 2.6 mol) and guanidine nitrate (48 g, 400 mmol) below 40° C. After stirring at room temperature for 15 minutes, MeOH was removed under vacuum, and the residue was heated at 100° C. for 1 hour. The mixture was then poured onto ice, exacted with $CHCl_3$, dried over $Na_2SO_4$ and filtered. Solvent evaporation gave a brown oil, which after CC with EtOAc gave 5.02 g (20%) of yellow solid 5-methoxy-2-aminopyrimidine. The structure was confirmed by $^1$H-NMR and EI-MS. EI-MS (m/z) 125 ($M^+$). Step 2: Under an Ar atmosphere at room temperature, $BBr_3$ (2.6 mL, 50 mmol) was added drop-wise to a solution of 5-methoxy-2-aminopyrimidine (1.25 g, 10 mmol) in 60 mL of benzene and the mixture was refluxed for 6 hours. After standing overnight at room temperature, the solvent was evaporated and the residue was carefully treated with 10 mL of ice cold $H_2O$. The pH of the solution was adjusted to 6-7 with 6 N HCl and then extracted with EtOAc. The EtOAc layers were washed with brine, dried over $Na_2SO_4$, and filtered. Solvent evaporation gave a yellow solid, which after CC using 20:1 $CHCl_3$:MeOH gave 840 mg (75%) of white solid 5-methoxy-2-amino-pyrimidine. The structure was confirmed by $^1$H-NMR and EI-MS. $^1$H NMR (DMSO-d$_6$) δ8.90 (s, 1H), 7.86 (s, 2H), 5.91 (s, 2H); EI-MS (m/z) 111 (M$^+$). Step 3: $K_2CO_3$ (276 mg, 2 mmol) was added to 222 mg of 5-methoxy-2-amino-pyrimidine (2 mmol) in 5 mL of MeCN, followed by BnBr (0.24 mL, 2 mmol). The mixture was refluxed for 3 hours. After cooling to room temperature, filtration, and solvent evaporation a red oil was obtained. This was purified by CC using 67:1 $CHCl_3$:MeOH to yield 300 mg (75%) of white solid 5-benzyloxy-2-amino-pyrimidine. The structure was confirmed by $^1$H-NMR. $^1$H NMR (CDCl$_3$) δ8.08 (s, 2H), 7.40-7.32 (m, 5H), 5.03 (s, 2H), 4.77 (brs, 2H). Step 4: The suspension of N-dimethylsulfamoyl-iminodiacetic acid (1.44 g, 6 mmol) in 8.0 mL of $Ac_2O$ was heated at 90° C. for 10 minutes until a clear solution was obtained. $Ac_2O$ was removed under vacuum at 60° C. to give a yellow solid, which was suspended in 20 mL of toluene. To this suspension was added a solution of 5-benzyloxy-2-amino-pyrimidine (1.0 g, 5 mmol) in 8 mL of acetone and the mixture was refluxed for 3.5 hours. After solvent evaporation, the remaining brown residue was dissolved in 30 mL of $Ac_2O$ and refluxed for 2 hours. After subsequent solvent evaporation and purification by CC with 100:1 $CHCl_3$:MeOH, 1.40 g (69%) of a white solid was obtained. The structure was confirmed by $^1$H-NMR. $^1$H NMR (CDCl$_3$) δ8.56 (s, 2H), 7.44-7.26 (m, 5H), 5.20 (s, 2H), 4.29 (s, 4H), 2.95 (s, 6H). Step 5: The white solid (2.0 g, 4.9 mmol) was dissolved in 100 mL of EtOAc was hydrogenated with 500 mg of 10% Pd/C catalyst at room temperature for 12 hours. After filtration and solvent evaporation, white solid JHX-4, recrystallized from EtOAc, was obtained (1.83 g (80%) mp 225-226° C.). The structure was confirmed by $^1$H-NMR, $^{13}$C-NMR, ESI-MS, and elemental analysis. $^1$H NMR (DMSO-d$_6$) δ11.0 (s, 1H), 8.45 (s, 2H), 4.39 (s, 4H), 2.85 (s, 6H); $^{13}$C NMR (CDCl$_3$) 168.9, 152.7, 146.9, 146.1, 50.0, 38.5; ESI-MS (m/z) 338 ([M+Na]$^+$).

Synthesis of 1-N,N'-dimethylsulfamoyl-4-(4,6-dimethoxy-2-pyrimidyl)piperazine (JHX-5)

Et$_3$N (0.73 mL, 5.2 mmol) was added to 1.0 g of piperazine-1-sulfonic acid dimethylamide (5.2 mmol) in 20 mL of THF. 2-chloro-4,6-dimethoxypyrimidine (0.9 g, 5.2 mmol) in 5 mL of THF was then added and the mixture was refluxed with stirring for 40 hours. After cooling, THF was removed under vacuum and the remaining yellow solid was dissolved in 300 mL of $CHCl_3$, washed with brine, dried over $Na_2SO_4$ and filtered. Solvent removal and CC with 1:1 $CHCl_3$:hexane gave 1.4 g (81%) of white JHX-5, mp 103-105° C. The structure was confirmed by $^1$H-NMR, $^{13}$C-NMR, EI-MS, and elemental analysis. $^1$H NMR (CDCl$_3$) δ5.41 (s, 1H), 3.86 (s, 6H), 3.89-3.86 (m, 4H), 3.28 (appt, J=4.88 Hz, 4H), 2.86 (s, 6H); EI-MS (m/z) 331 (M$^+$).

Synthesis of 1-N,N'-dimethylsulfamoyl-4-(4,6-dimethoxy-5-hydroxy-2-pyrimidyl)piperazine (JHX-6)

To a solution of 1.66 g JHX-5 (1.66 g, 5 mmol) in 40 mL of THF at −78° C. and under an Ar atmosphere was added 0.3 mL of n-BuLi (7 mmol). After 3 hours stirring at −60° C., the Ar atmosphere was replaced with oxygen. The reaction mixture was then gradually warmed to room temperature and stirring was continued for an additional for 6 hours. After adjusting the pH to 6-7 with dilute HCl, THF was removed by evaporation and the remaining aqueous layer was extracted with $CHCl_3$. The $CHCl_3$ layers were washed with brine, dried over $Na_2SO_4$ and filtered. Solvent evaporation gave a yellow solid, which was purified by CC with 1:1:2 $CHCl_3$:EtOAc:hexane to yield 530 mg (30%) of JHX-6, mp 113-114° C. The structure was confirmed by $^1$H-NMR, EI-MS, and elemental analysis. $^1$H NMR (CDCl$_3$) δ4.21 (s, 1H), 3.95 (s, 6H), 3.76 (s, 4H), 3.29 (s, 4H), 2.86 (s, 6H); EI-MS (m/z) 347 (M$^+$).

Synthesis of 1-N,N'-dimethylsulfamoyl-4-(4,6-dimethoxy-2-pyrimidyl)piperazine-2,6-dione (JHX-7)

Step 1: A suspension of N-benzyliminodiacetic acid (8.9 g, 40 mmol) in 42 mL of $Ac_2O$ was refluxed for 20 minutes until clear. $Ac_2O$ was removed under vacuum at 60° C. and the remaining yellow oil was dissolved in 90 mL of toluene. A solution of 2-amino-4,6-dimethoxypyrimidine (6.2 g, 40 mmol) dissolved in 30 mL of acetone was then added and the reaction mixture was refluxed for 12 hours. After evaporating the acetone, the reaction mixture was allowed to stand at room temperature until a white solid crystallized (ca. 20 minutes). The filtered solid was washed with toluene and Et$_2$O to yield 12.89 g (90%) of a white solid. $^1$H NMR (DMSO-d$_6$) δ10.18 (s, 1H), 7.38-7.25 (m, 5H), 5.89 (s, 1H), 3.85 (s, 6H), 3.84 (s, 2H), 3.61 (s, 2H), 3.44 (s, 2H). Step 2: A suspension of the white solid (12.89 g, 35.8 mmol) in 90 mL of $Ac_2O$ was refluxed for 4 hours until a clear red solution was obtained. After cooling to room temperature the $Ac_2O$ was removed under vacuum at 60° C. The remaining reside was recrystallized from EtOAc to give 9.33 g (76%) of a white solid. $^1$H NMR (CDCl$_3$) δ 7.39-7.31 (m, 5H), 6.07 (s, 1H), 3.93 (s, 6H), 3.74 (s, 2H), 3.56 (s, 4H). Step 3: 2.72 g (8.0 mmol) of the white solid dissolved in a mixture of a mixture of 50 mL MeOH and 40 mL EtOAc was hydrogenated with 8.26 mg of 10% Pd/C catalyst for 12 hours at room temperature. After filtration, and evaporation of solvent, the remaining white solid was purified by CC using 60:1 $CHCl_3$:MeOH as eluent to give 1.47 g (74%) of white solid. $^1$H NMR (DMSO-d$_6$) δ 6.40 (s, 1H), 3.87 (s, 6H), 3.69 (s, 4H), 3.44 (s, 1H). Step 4: $KHCO_3$ (853 mg, 8.5 mmol) was added to a solution of 21 (1.41 g, 5.68 mmol) dissolved in 30 mL of MeCN, followed by dimethylsulfamoyl chloride (8.5 mL, 8.5 mmol). The mixture was heated to 60° C. for 24 hours and then cooled to room temperature. After filtration and solvent evaporation the remaining pink solid was purified by CC using $CHCl_3$ as eluent to yield 1.57 g (77%) of white solid JHX-7, mp 200-202° C. $^1$H NMR (CDCl$_3$) δ6.10 (s, 1H), 4.30 (s, 4H), 3.92 (s, 6H), 2.967 (s, 6H); $^{13}$C NMR (CDCl$_3$) 172.8, 166.7, 152.8, 90.5, 54.7, 49.4, 38.2; ESI-MS (m/z) 382 ([M+Na]$^+$).

Synthesis of 1-N,N'-dimethylsulfamoyl-4-(4,6-dimethoxy-5-hydroxy-2-pyrimidyl)piperazine-2,6-dione (JHX-8)

Step 1: To a stirred suspension of 10.44 g 2-chloride-4,6-dimethoxypyrimidine (60 mmol) in 200 mL of THF under argon at −78° C. was added drop-wise a solution of LDA (2 M in THF/heptane/ethyl benzene, 60 mL, 120 mmol). To a separate round-bottomed flask −78° C. under argon containing t-butyl hydroperoxide (5.5 M in decane, 22.7 mL, 125 mmol) in 150 mL of THF was added a solution of n-BuLi (1.6 M in hexane, 78 mL, 125 mmol). Then, after stirring for 1 hour, the hydroperoxide anion solution was added via a double-ended needle to the aromatic anion. The temperature was gradually raised to 0° C. with stirring continued an additional 3 hours. The reaction was quenched with 6N HCl untie a pH of 7 was obtained. After THF evaporation the remaining aqueous layer was extracted with $CHCl_3$. The $CHCl_3$ layers were washed with brine, dried over $Na_2SO_4$, and filtered. Removal of solvent and subsequent purification by CC using 10:1 hexane:EtOAc gave 10.67 g (93.4%) of a white solid. The structure was confirmed by $^1$H-NMR and $^{13}$C-NMR. $^1$H NMR ($CDCl_3$) δ 4.93 (s, 1H), 4.05 (s, 6H). $^{13}$C NMR ($CDCl_3$) 158.1, 146.7, 123.0, 55.1. Step 2: $K_2CO_3$ (10.0 g, 70 mmol) was added to the white solid (13.24 g, 69.5 mmol) dissolved in 200 mL of MeCN followed by BnBr (8.3 mL, 69.5 mmol). After 14 hours stirring at room temperature, the reaction was stopped by addition of water. MeCN was evaporated the remaining aqueous layer was extracted with $CHCl_3$. The combined $CHCl_3$ layers were washed with brine, dried over $Na_2SO_4$, and filtered. Removal of the solvent followed by CC using 25:1 hexane:EtOAc gave 16.57 g (85%) of a benzyloxy. The structure was confirmed by $^1$H-NMR and $^{13}$C-NMR. $^1$H NMR ($CDCl_3$) δ 7.41-7.31 (m, 5H), 5.00 (s, 2H), 3.98 (s, 6H) $^{13}$C NMR ($CDCl_3$) 163.6, 150.5, 136.4, 128.5, 128.4, 128.3, 124.4, 74.8, 54.0. Step 3: A mixture of the benzyloxy (3.18 g, 11.33 mmol), $BnNH_2$ (2.2 mL, 20 mmol) and $K_2CO_3$ (1.66 g, 12 mmol) in dioxane (60 mL) was refluxed for 4 days. The reaction was filtered and the filtrate concentrated in vacuo to give a yellow oil, which after CC with 25:1 to 10:1 hexane:EtOAc gave 2.54 g (64%) of a white solid. The structure was confirmed by $^1$H-NMR and $^{13}$C-NMR. $^1$H NMR ($CDCl_3$) δ 7.45-7.24 (m, 10H), 5.10 (br s, 1H), 4.85 (s, 2H), 4.55 (d, J=5.5 Hz, 2H), 3.86 (s, 6H). $^{13}$C NMR ($CDCl_3$) 163.5, 156.0, 139.7, 137.5, 128.5, 128.4, 128.1, 127.8, 127.6, 127.1, 117.7, 75.2, 53.7, 45.9. Step 4: The white solid (2.54 g, 7.24 mmol) in 40 mL of MeOH was hydrogenated for 12 hours at room temperature in the presence of 635 mg of 10% Pd/C catalyst. After filtration, and solvent evaporation, a white solid was obtained which after CC using 50:1 $CHCl_3$:MeOH yielded 1.21 g (98%) of 2-amino-4-hydroxy-2,6-dimethoxypyrimidine. The structure was confirmed by $^1$H-NMR. $^1$H NMR ($CDCl_3$) δ 4.50 (s, 2H), 4.30 (s, 1H), 3.93 (s, 6H). Step 5: To 4.16 g of 2-amino-4-hydroxy-2,6-dimethoxypyrimidine (24.3 mmol) in MeOH (240 mL) was added $K_2CO_3$ (3.5 g, 25 mmol), and followed by BnBr (3.0 mL, 25 mmol). After 12 hours stirring at room temperature, water was added to the reaction mixture. MeOH was evaporated and the water layer was extracted with $CHCl_3$. The combined $CHCl_3$ layers were washed with brine, dried over $Na_2SO_4$, and filtered. Removal of $CHCl_3$ gave a yellow solid, which after purification by CC with 10:1 to 2:1 hexane:EtOAc yielded 5.14 g (81%) of 2-amine-4,6-dimethoxy-5-benzyloxypyrimidine. The structure was confirmed by $^1$H-NMR. $^1$H NMR ($CDCl_3$) δ 7.44-7.27 (m, 5H), 4.86 (s, 2H), 4.60 (s, 2H), 3.87 (s, 6H). Step 6: A suspension of 5.6 g of N-dimethylsulfamoyliminodiacetic acid (23.4 mmol) in 25 mL of $Ac_2O$ was heated to 80° C. for 5 minutes until a clear. $Ac_2O$ was removed in vacuo at 60° C. to give a red oil, which was suspended in 50 mL of toluene. A solution of 4.07 g of 2-amine-4,6-dimethoxy-5-benzyloxypyrimidine (15.6 mmol) in 25 mL of acetone was then added and the mixture was refluxed for 18 hours. After removing the solvent, the remaining brown residue was dissolved in 60 mL of $Ac_2O$ and refluxed for 4 hours. The brown solid again obtained by removing the solvent was purified by CC using 100:1 $CHCl_3$:MeOH to yield 2.97 g (41%) of a pale yellow solid. The structure was confirmed by $^1$H-NMR and $^{13}$C-NMR. $^1$H NMR ($CDCl_3$) δ 7.46-7.32 (m, 5H), 5.05 (s, 2H), 4.29 (s, 4H), 3.95 (s, 6H), 2.96 (s, 6H); $^{13}$C NMR ($CDCl_3$) 166.8, 164.0, 144.9, 136.6, 128.4, 128.3, 128.2, 128.1, 125.8, 74.8, 54.9, 49.4, 38.2. Step 7: 10% Pd/C catalyst (314 mg) was added to 1.57 g of the pale yellow solid (3.38 mmol) in 50 mL of EtOAc and the mixture was hydrogenated at room temperature for 5.5 hours. After filtration and removal of solvent, the remaining solid was purified by CC using 80:1 $CHCl_3$:MeOH to yield 1.15 g (91%) of white solid JHX-8 mp 222-224° C. The structure was confirmed by $^1$H-NMR, $^{13}$C-NMR, ESI-MS, and elemental analysis. $^1$H NMR ($CDCl_3$) δ 9.67 (s, 1H), 4.44 (s, 4H), 3.88 (s, 6H), 2.51 (s, 6H); $^{13}$C NMR ($CDCl_3$) 168.1, 159.4, 140.9, 124.7, 54.7, 49.3, 37.9; ESI-MS (m/z) 398 ([M+Na]$^+$); Anal. Calcd for $C_{12}H_{17}N_5O_7S$: C, 38.40; H, 4.56; N, 18.66; S, 8.54. Found: C, 38.60; H, 4.66; N, 18.49; S, 8.58.

EXAMPLE II

Chelation Studies

The relative amount of ions bound by JHX-1-JHX-8 was determined by electrospray ionization mass spectrometry (ESI-MS) according to the method of Baron and Hering (Baron and Hering (1998) Spectrometry J. Environ. Qual., 27:844-850). In this method solutions containing $Fe^{2+}$, $Fe^{3+}$, $Cu^{1+}$, $Cu^{2+}$, $Zn^{2+}$, $Ca^{2+}$, $Mg^{2+}$ were mixed with compound in ratios of 10:1, 1:1, and 1:10. After 45 minutes of mixing, each solution was directly infused into the MS with constant ionization energy and the relative decreases of the parent peaks in these solutions were determined. Table 1 below illustrates that only compounds JHX-3, 4, 7, and 8, which possess the required piperazine-2,6-dione groups, bind ions with a binding order of $Cu^{1+}=Cu^{2+}>Fe^{2+}=Fe^{3+}>Zn^{2+}$ observed. No binding with $Ca^{2+}$ or $Mg^{2+}$ was observed, indicating that the binding is selective. FIG. 3 illustrates ion binding with increased $Fe^{+2}$ concentrations results in decreased compound parent peak heights by ESI-MS when compounds contain appropriate functional groups for metal ion chelation.

TABLE 1

| % Parent Peak Remaining at 10:1 Solution of Metal:Compound | | | | | | | |
|---|---|---|---|---|---|---|---|
| Compound | Ion Solutions | | | | | | |
| JHX | $Fe^{2+}$ | $Fe^{3+}$ | $Cu^{1+}$ | $Cu^{2+}$ | $Zn^{2+}$ | $Ca^{2+}$ | $Mg^{2+}$ |
| 1 | 100.0 | 100.0 | 100.0 | 100.0 | 100.0 | 100.0 | 100.0 |
| 2 | 100.0 | 100.0 | 100.0 | 100.0 | 100.0 | 100.0 | 100.0 |
| 3 | 8.1 | 10.0 | 3.6 | 4.4 | 15.3 | 100.0 | 100.0 |
| 4 | 6.9 | 8.2 | 4.2 | 3.0 | 12.7 | 100.0 | 100.0 |
| 5 | 100.0 | 100.0 | 100.0 | 100.0 | 100.0 | 100.0 | 100.0 |
| 6 | 100.0 | 100.0 | 100.0 | 100.0 | 100.0 | 100.0 | 100.0 |
| 7 | 7.3 | 7.6 | 4.1 | 3.4 | 13.8 | 100.0 | 100.0 |
| 8 | 7.5 | 8.2 | 4.0 | 3.6 | 14.6 | 100.0 | 100.0 |

In Vitro Lens Cell Studies

The SRA-1 human lens epithelium cell line (Ibaraki et al. (1998) Exp. Eye Res., 67:577-85) was used to evaluate the antioxidant activity of JHX-1-8. These cells were cultured in DMEM media containing 10% fetal bovine serum (FBS), glutamine, $NaHCO_3$, penicillin, and streptomycin at 37° C. in humidified atmosphere of 5% $CO_2$ and 95% air until subconfluent (2-4 days). The cells were passaged when 80-90% confluent by treatment with trypsin-EDTA. The cells were plated at a density of $1\times10^4$ cells onto 96-well plates or $1\times10^6$ cells onto 100-mm dishes. ROS levels/effects in cells treated with JHX-1-8 were compared to similar cells treated with the water soluble Vitamin E derivative, Trolox (antioxidant control) or no drug (control).

ROS Staining

The compounds were initially screened for antioxidant activity in 24 hour cultured SRA-1 human lens epithelial cells. Reactive oxygen species (ROS) in these cells were generated through both the Fenton reaction in which 0.1 mM $Fe^{2+}$ and 0.1 mM hydrogen peroxide were added to the culture media, or by culturing the lens with 10 mM homocysteine which induces endoplasmic reticular (ER) stress that results in the unfolded protein response (UPR) that subsequently generates the ROS. ROS were visualized with 2',7'-dichlorodihydrofluorescein diacetate (DCF) staining. More specifically, after 24 hours of incubation, all cells were washed 2× with PBS and then incubated at room temperature for 1 hour with 10 μM $H_2$DCF-DA (Invitrogen) stain. Fluorescent ROS staining was analyzed by quantifying pixel intensities of images obtained by fluorescent microscopy. As illustrated below in FIGS. 4A and 4B, compounds with chelating groups only produced a dose-dependent reduction in Fenton Reaction generated ROS. Compounds possessing free radical scavenging activity reduced ROS generated by both methods. Indeed, homocysteine activates ER stress which subsequently initiates ROS through an Unfolded Protein Response (UPR). Because this in not metal dependent, only analogs (JHX-2, 4, 6, 8) possessing an —OH FRS group reduced ROS staining similar to that with Trolox. When ROS was generated with $H_2O_2$ and $Fe^{2+}$, decreased staining was also observed with JHX-3 and JHX-7 which only possess chelating (CHL) groups. Compounds possessing both CHL and FRS groups were better than Trolox.

Cell Viability

The MTS cell viability assay (3-[4,5-dimethylthiazol-2-yl]-5-[3-carboxymethoxyphenyl]-2-[4-sulfophenyl]-2H-tetrazolium) was used to assess the ability of JHX-1-8 to protect against ROS-induced cell death. Cells were cultured in 96-well plates and exposed for 2 hours to media containing 1.0 mM $H_2O_2$ (FIG. 5A) or Fenton reagents (1.0 mM $H_2O_2$ and 1.0 mM $Fe^{2+}$, FIG. 5B) with/without 1 mM JHX-1-8 or Trolox. Viability was measured as the absorbance of MTS stain at 490 nm 1 hour after the addition of 20 μL of CellTiter 960 AQueous One Solution Cell Proliferation Assay to each well. The results were normalized to blank control (100%) since absorbance is directly proportional to the living cell population. The results were similar to those observed in the previous experiment with analogs possessing the FRS group (JHX-2, 4, 6, 8) protecting against $H_2O_2$ induced loss of cell viability. In the presence of Fenton, human lens epithelial cells (HLEC) viability was increased compared to controls by 10% with CHL compounds, 15% with FRS compounds, and 20% in compounds with both groups. Trolox increased viability by 15%.

Cellular Reduced Glutathione (GSH) Levels

Reduced glutathione (GSH) is a protective cellular antioxidant whose levels rapidly decrease in response to oxidative stress. Cellular GSH levels were measured in cells cultured in 100-mm dishes after 2 hours exposure to media containing either 1.0 mM $H_2O_2$ or 1.0 mM Fenton reagents with/without 1 mM compounds JHX-1-8 or Trolox. After the 2 hours incubation, the cells were homogenized and protein levels were measured according to Bradford (Bradford, M. M. (1976) Anal. Biochem., 72:248-54). The cell homogenates were then deproteinized with equal volumes of 20% TCA and GSH levels were measured at 412 nm according to the DTNB method (5,5'-dithiobis(2-nitrobenzoic acid) (Lou and Dickerson (1992) Exp. Eye Res., 55:889-96). GSH levels were expressed as nmol GSH/mg protein, with values normalized to the blank control (100%). GSH remained unchanged (17.2 nmol GSH/mg protein) when cells were cultured with JHX-1-8 in the absence of $H_2O_2$ indicating that these compounds are not pro-oxidants at the concentrations utilized. As summarized in FIGS. 6 and 7, protection of cellular GSH levels by these compounds was similar to protection from ROS demonstrated with $H_2$DCF-DA ROS staining and MTA cell viability staining. In cells exposed to Fenton reagents, protection against ROS by our compounds containing CHL, FRS, or both groups resulted in 15-30% (2.6-5.2 nmol/mg protein) increases in cellular GSH levels.

Drug Levels in Target Tissues

To determine whether JHX-4 and JHX-8 can reach the target tissues of lens, retina and brain after oral administration, two groups of 4 young (100 g) Sprague Dawley rats were administered rat chow containing 0.05% of either drug for 6 days. Feeding studies indicated that this corresponded to an average dose of 80±10 mg/kg/day. Lens and posterior segments were homogenized in glass homogenizers in ice-cold PBS, pH 7.4, after addition of an aliquot of JHX-1 as an internal standard. The homogenates were deproteinized with 48 mM NaF and centrifuged. The supernatant was extracted with acetone. The acetone extract was evaporated under vacuum and the residue was dissolved in acetonitrile. Whole brains were similarly extracted; however, brain homogenates were deproteinized with equal amounts of 0.3 N $Na_2SO_4$ and 0.3 N $Ba(OH)_2$. Drug levels were measured by reverse-phase HPLC with a Phenomenex LUNA 5 μm C18 column and an isocratic elution of 1:1 MeOH:Water. Detection was conducted at 245 nm and compound levels were quantified using standard curves. Lens and retinal drug levels were 200±11 and 1373±38 ng/mg protein for JHX-4 and 90±5 and 1060±12 ng/mg protein for JHX-8 respectively. Only trace amounts of either compound were detected in the brain.

Cataract Formation in Diabetic Rats

Diabetes was induced in 100 g Sprague Dawley rats with streptozotocin injection (75 mg/kg) and all rats with blood sugar levels >300 mg/dL were divided into 4 groups of 8 rats each. One group received only standard rat chow (untreated diabetic) while each of the other groups received chow containing either 0.0125% ARI Al1576, 0.025% JHX-4 or 0.025% JHX-8. Lens changes were monitored by at 3-5 day intervals by slit lamp following tropicamide mydriasis. As summarized in FIGS. 8A-8C, vacuole formation began by 14 days in the untreated diabetic group with cortical opacities observed by 29 days and mature cataracts by 44 days. No lens changes were observed in the AL1576 treated rats. In the two antioxidant treated groups, vacuole formation was delayed by 19 and 11 days by JHX-4 and JHX-8, respectively, and cortical cataracts by 9 and 3 days, respectively. At the end of the study (47 days) all rats were equally diabetic with $HbA_{1C}$ levels >11.9%. All eyes were enucleated and lens sorbitol levels were measured as previously described (Kador et al. (2007) J. Ocul. Pharmacol. Ther., 23:116-23). No sorbitol was present in the ARI treated lenses while levels in the untreated and antioxidant treated eyes were similar (FIG. 9). Tissue levels of JHX-4 and -8 in the lens, neural retina and brain were determined after 47 days of feeding as described above (FIG. 10). Lens levels again were higher in the JHX-4 group suggesting that the delays observed were proportional to the lens levels of drug achieved. Overall drug levels in both the lens and retina were ca. 3-fold higher in the diabetic rats with brain levels also now present. This increase may be due to either an accumulation of drug, or increased permeability of tissues and the BBB to drug in streptozotocin diabetic rats (Mooradian et al. (2005) Diabetes, 54:2977-82).

EXAMPLE III

Irradiation Cataracts

Cataracts were induced by whole head gamma irradiation in 24 male Long Evans (150-200 g) rats. Prior to irradiation, these were randomly divided into 4 groups with Group 1 receiving only radiation, Group 2 receiving Pantethine (1 g/kg i.p.) injection prior to irradiation as described (Clark et al. (1996) Exp. Eye Res., 62:75-84), Group 3 receiving 0.025 wt % JHX-4 in their chow and Group 4 receiving 0.025 wt % JHX-8 in their chow. Because of the amount of drug required for this long-term study, the percentage of JHX-4 and JHX-8 utilized was ½ of the dose used in the diabetic study. Chow treatments were initiated 14 days prior to irradiation while Pantethine was administered intraperiotoneally 45 minutes prior to irradiation. Gamma radiation (6000 Curie Cobalt-60 Source, UNMC Experimental Radiation Facility) was delivered to the whole head of unanesthetized, restrained rats at a dose rate of dose 0.341 Gy/minute for a total dose of 15 Gy. Lens changes were monitored every 7 days by portable slit lamp and recorded on a scale from 0-6 with 0: Clear, 1: Posterior subcapsular haze, 2: Spokes, suture enhancement and powdery posterior subcapsular deposits, 3: Prominent posterior subcapsular punctate opacities with spokes and suture enhancement, 4: Posterior subcapsular opacity blocks appearance of retinal vessels, 5: Start cortical involvement, 6: Total lens opacity, visible with naked eye. Since whole head irradiation results in a temporary loss of salivary gland function, all rats received Nutra-Gel (Bio-Serv) with/without JHX-4 or -8 for the first 66 days. Subsequently, all rats received standard rat chow with/without JHX-4 or -8.

As anticipated, whole head irradiation resulted in altered consumption of chow (FIG. 11) with a resulting reduction of body weight (FIG. 12). However, chow consumption measured at two day intervals immediately after irradiation showed a marked reduction in feeding in only the Pantethine and untreated rats (dashed oval area) with a gradual increase to JHX-4 and -8 levels by the Pantethine group at 16 days post irradiation. The consumption measurements were verified by decreased body weights. While all groups were of equal weight at the day of irradiation (dashed oval area), the body weights of both the Panthine and untreated group significantly decreased after irradiation compared to the JHX-4 and -8 treated rats (FIG. 12). These results strongly indicate that both JHX-4 and -8 provided systemic protection of the salivary gland after whole head irradiation.

Whole head 15 Gy irradiation of pigmented Long Evans rats resulted in a gradual formation of lens opacities (FIG. 13). The initial lens change began approximately 60 days post irradiation as the formation of a diffuse prominent posterior capsular (PSC) clouding (haze) followed by the appearance of spokes, suture accentuation, and a progressive increase in PSC opacification (ca. 70 days) that resulted in the appearance of punctuate opacities (ca. 80 days) that eventually became dense enough to block visualization of the retina (ca. 90 days). Gradually, cortical opacities developed (ca. 120 days) that eventually resulted in total lens opacification (ca. 160 days). Treatment with Pantethine and JHX-4 and -8 delayed the appearance of these lens opacities; however, the effect of Pantethine was minimal (FIG. 13). Compared to untreated rats, treatment with Pantethine and JHX-4 and -8 delayed the average (50% in all animals) formation of PSC punctuate opacities by 23, 53 and 58 days, respectively (FIG. 14A) and lens PSC opacities by 4, 38 and 47 days, respectively (FIG. 14B).

The above demonstrated efficacy could be increased with increased administration of JHX-4 and JHX-8. No apparent toxic effects were observed in either diabetic or irradiated rats. In fact, administration of JHX-4 and -8 to the irradiated rats appeared to have beneficial systemic effects in reducing post-irradiation weight loss and the overall appearance of the rats.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. A compound of the formula:

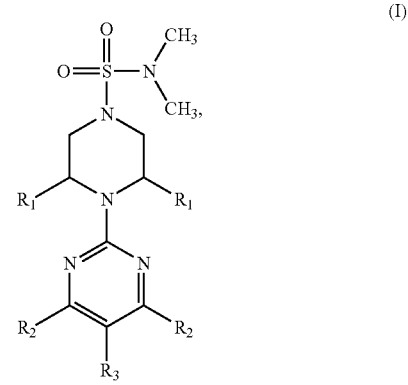

(I)

wherein $R_1$ is =O or comprises two moieties independently selected from the group consisting of H, halo, thiol, carboxy, nitro, amino, cyano, hydroxyl, alkyl, and aryl, wherein $R_2$ is selected from the group consisting of H, halo, thiol, carboxy, nitro, amino, cyano, hydroxyl, alkyl, and aryl, and wherein $R_3$ is OH.

2. The compound of claim 1, wherein at least one $R_2$ is selected from the group consisting of H, halo, thiol, carboxy, nitro, amino, cyano, hydroxyl, and a lower alkyl.

3. The compound of claim 1, wherein at least one $R_1$ is =O.

4. The compound of claim 1, wherein at least one $R_1$ is H, H or =O; and at least one $R_2$ is selected from the group consisting of H, —R, —OR, —SR, and —NHR, wherein R is H or a lower alkyl.

5. The compound of claim 1, wherein at least one $R_1$ is =O; and at least one $R_2$ is selected from the group consisting of H, —R, —OR, —SR, and —NHR, wherein R is H or a lower alkyl.

6. The compound of claim 1, wherein both $R_1$ groups are H,H and both $R_2$ groups are H.

7. The compound of claim 1, wherein both $R_1$ groups are =O and both $R_2$ groups are H.

8. The compound of claim 1, wherein both $R_1$ groups are H, H and both $R_2$ groups are —$OCH_3$.

9. The compound of claim 1, wherein both $R_1$ groups are =O and both $R_2$ groups are —$OCH_3$.

10. A composition comprising at least one compound of claim 1 and at least one pharmaceutically acceptable carrier.

* * * * *